(12) United States Patent
Laustsen et al.

(10) Patent No.: US 11,286,292 B2
(45) Date of Patent: Mar. 29, 2022

(54) BIOREACTOR ARRANGEMENT AND CONTINUOUS PROCESS FOR PRODUCING AND CAPTURING A BIOPOLYMER

(71) Applicant: CMC BIOLOGICS A/S, Soborg (DK)

(72) Inventors: Mads Laustsen, Gentofte (DK); Simon Bergmann, Hellerup (DK)

(73) Assignee: CMC BIOLOGICS A/S, Soborg (DK)

(*) Notice: Subject to any disclaimer, the term of this patent is extended or adjusted under 35 U.S.C. 154(b) by 86 days.

(21) Appl. No.: 15/117,059

(22) PCT Filed: Jan. 29, 2015

(86) PCT No.: PCT/EP2015/051797
§ 371 (c)(1),
(2) Date: Aug. 5, 2016

(87) PCT Pub. No.: WO2015/117883
PCT Pub. Date: Aug. 13, 2015

(65) Prior Publication Data
US 2016/0349220 A1    Dec. 1, 2016

(30) Foreign Application Priority Data

Feb. 7, 2014 (EP) .................... 14154324
Mar. 27, 2014 (EP) .................... 14161900

(51) Int. Cl.
*C07K 16/00* (2006.01)
*G01N 30/46* (2006.01)
(Continued)

(52) U.S. Cl.
CPC .......... *C07K 16/00* (2013.01); *B01D 15/1864* (2013.01); *B01D 15/1885* (2013.01);
(Continued)

(58) Field of Classification Search
CPC .......... B01D 15/1864; B01D 15/1885; B01D 15/20; B01D 15/3804; B01D 15/424;
(Continued)

(56) References Cited

U.S. PATENT DOCUMENTS 5,362,642 A    11/1994    Kern
7,947,813 B2   5/2011     Fahrner
(Continued)

FOREIGN PATENT DOCUMENTS

EP    2014760    5/2010
EP    2451963    4/2014
(Continued)

OTHER PUBLICATIONS

"Process Analytical Equipment for Monitoring, Control and Cost Optimization of Inline Dilution Processes turning science into solutions", Jan. 1, 2012 (Jan. 1, 2012), Retrieved from the Internet: URL:http://www.sartorius.de/fileadmin/fm-dam/sartoriusjmedia/Bioprocess-Solutions/Process_Analytical_Tec (Year: 2012).*
(Continued)

*Primary Examiner* — Latosha Hines
(74) *Attorney, Agent, or Firm* — Cheryl H. Agris; Agris & von Natzmer, LLP

(57) ABSTRACT

The present invention relates to a bioreactor arrangement for producing a biopolymer expressed by a cell and a continuous process for a capturing the biopolymer employing two chromatography units operated in series or independently.

9 Claims, 2 Drawing Sheets

(51) Int. Cl.
| | |
|---|---|
| G01N 30/88 | (2006.01) |
| C07K 1/36 | (2006.01) |
| B01D 15/18 | (2006.01) |
| B01D 15/20 | (2006.01) |
| B01D 15/38 | (2006.01) |
| B01D 15/42 | (2006.01) |
| C12M 1/26 | (2006.01) |

(52) U.S. Cl.
CPC ......... *B01D 15/20* (2013.01); *B01D 15/3804* (2013.01); *B01D 15/424* (2013.01); *C07K 1/36* (2013.01); *C12M 33/00* (2013.01); *G01N 30/468* (2013.01); *G01N 30/88* (2013.01); *C07K 2317/55* (2013.01); *C07K 2317/622* (2013.01); *G01N 2030/8831* (2013.01)

(58) Field of Classification Search
CPC ...... C07K 16/00; C07K 1/36; C07K 2317/55; C07K 2317/622; C12N 33/00; G01N 2030/8831; G01N 30/468; G01N 30/88
See application file for complete search history.

(56) References Cited

U.S. PATENT DOCUMENTS

| | | | |
|---|---|---|---|
| 8,271,139 B2 | 9/2012 | Bellafiore | |
| 8,679,778 B2 * | 3/2014 | Laustsen | ............... C07K 16/00 435/41 |
| 2011/0073548 A1 * | 3/2011 | Williams | ............... G01N 30/28 210/739 |
| 2012/0156783 A1 | 6/2012 | Kubiak | |
| 2013/0280788 A1 | 10/2013 | Skudas | |
| 2013/0323841 A1 | 12/2013 | Kruglick | |
| 2015/0118753 A1 | 4/2015 | Brau | |
| 2015/0232505 A1 | 8/2015 | Konstantinov | |

FOREIGN PATENT DOCUMENTS

| | | | |
|---|---|---|---|
| WO | 2008153472 | 12/2008 | |
| WO | 2010056584 | 5/2010 | |
| WO | 2011003153 | 1/2011 | |
| WO | 2012074481 | 6/2012 | |
| WO | WO-2012074481 A1 * | 6/2012 | ......... B01D 15/3847 |
| WO | 2015075070 | 5/2015 | |
| WO | 2015117883 | 8/2015 | |
| WO | 2015117884 | 8/2015 | |
| WO | 2015158696 | 10/2015 | |

OTHER PUBLICATIONS

Related PCT appln. No. PCT/EP2015/058037 (published as WO 2015/158696), International Search Report and Written Opinion dated Jun. 17, 2015.
Related PCT Appln. No. PCT/EP2015/051801(published as WO2015/117884), International Preliminary Report on Patentability (IPRP), dated Aug. 9, 2016.
Related PCT Appln. No. PCT/EP2015/051801 (published as WO2015/117884), International Search Report, dated Apr. 28, 2015.
Related PCT Appln. No. PCT/EP2015/051797 (published as WO2015/117883), IPRP, Aug. 9, 2016.
Related PCT Appln. No. PCT/EP2014/075019 (published as WO2015/075070), IPRP, Jan. 23, 2015.
"Process Analytical Equipment for Monitoring, Control and Cost Optimization of Inline Dilution Processes turning science into solutions", Jan. 1, 2012 (Jan. 1, 2012), XP055118436, Retrieved from the Internet: URL:http://www.sartorius.de/fileadmin/fm-dam/sartorius_media/Bioprocess-Solutions/Process_Analytical_Technology/Application_Notes/ Appl_PAT_Equipment_for_Inline_Dilution_Processes_W--1125-e.pdf.
Response to EP Office Action for related EP Appln. No. 15714846.1 dated Jun. 6, 2017.
Related PCT appln. No. PCT/EP2015/058037 (published as WO 2015/158696 A1), IPRP dated Oct. 18, 2016.
U.S. Appl. No. 15/303,735, Office Action dated Apr. 12, 2018.
U.S. Appl. No. 15/303,735, Office Action dated Jun. 30, 2017.
Related EP appln. No. EP15704231.8, amended claims dated Jun. 22, 2017.
Related EP appln. No. EP15702220.3, response to written opinion, dated Apr. 6, 2017.
Related U.S. Appl. No. 15/117,059, Restriction Requirement dated Jun. 25, 2018.
U.S. Appl. No. 15/117,059, Office Action dated Sep. 13, 2018.
Related EP appln. No. 14 799795.1, communication dated Jun. 30, 2016.
Related EP appln No. 14 799795.1, response to communication dated Jun. 30, 2016, submitted Jan. 6, 2017.
U.S. Appl. No. 15/117,019, Restriction Requirement dated Jun. 25, 2018.
U.S. Appl. No. 15/117,019, Office Action dated Sep. 7, 2018.
U.S. Appl. No. 15/037,765, Restriction Requirement dated Jun. 6, 2017.
U.S. Appl. No. 15/037,765, Office Action dated Nov. 6, 2017.
Related U.S. Appl. No. 15/117,059, Interview Summary, dated Dec. 13, 2019.
Related U.S. Appl. No. 15/117,059, Office Action dated Jun. 13, 2019.
Related U.S. Appl. No. 15/117,059, Office Action dated Jan. 10, 2020.
U.S. Appl. No. 15/972,146, Office Action dated Mar. 19, 2021.
U.S. Appl. No. 15/972,146, Interview Summary dated Dec. 17, 2020.
U.S. Appl. No. 15/972,146, Office Action dated Jun. 19, 2020.
U.S. Appl. No. 15/972,146, Office Action dated Jan. 2, 2020.
U.S. Appl. No. 15/117,019, Office Action dated Apr. 29, 2021.
U.S. Appl. No. 15/117,019, Office Action dated Oct. 16, 2020.
U.S. Appl. No. 15/303,735, Notice of Allowance dated Jun. 14, 2019.
U.S. Appl. No. 15/303,735, Interview Summary dated Jun. 3, 2019.
U.S. Appl. No. 15/303,735, Office Action dated Apr. 11, 2018.
U.S. Appl. No. 15/972,146, Interview Summary dated Jul. 12, 2021.
Related EP appln. No. 14799795.1, communication dated Apr. 21, 2021.
Related EP appln. No. 14799795.1, communication dated Apr. 3, 2019.
Related EP appln. No. 14799795.1, response to communication dated Apr. 3, 2019, submitted Jul. 25, 2019.
U.S. Appl. No. 15/117,059, Interview Summary dated Sep. 13, 2021.
U.S. Appl. No. 15/117,059, Office Action dated May 12, 2021.
Related EP appln. No. 15702220.3, Communication dated Apr. 20, 2021.

* cited by examiner

BIOREACTOR ARRANGEMENT AND CONTINUOUS PROCESS FOR PRODUCING AND CAPTURING A BIOPOLYMER

FIELD OF THE INVENTION

The present invention relates to a bioreactor arrangement and a continuous method for producing and capturing a biopolymer using the bioreactor arrangement. The methods of the present invention are suitable for use in a manufacturing process for preparing a protein or polypeptide, in particular for preparing an active pharmaceutical ingredient for a pharmaceutical product.

BACKGROUND OF THE INVENTION

Traditionally, bacterial, yeast and mammalian cells for e.g. protein production are primarily cultured as suspension cultures in bioreactors, also called fermenters. In such bioreactors the environmental conditions can be precisely controlled by manipulating the supply of nutrients to the cells and the removal of waste materials, and a stirring means may stir the culture medium within the reactor to provide for a homogeneous distribution of the cells.

The bioreactor may be operated as a closed system in a batch or fed-batch process or as a continuous system in a so-called chemostat or perfusion process.

In a batch operation the culture medium usually contains a medium with the necessary nutrients, for example glucose, vitamins, amino acids and minerals. During fermentation, these are consumed so that the medium becomes more and more deprived in nutrients. At the same time, the concentration of waste products increases, which ultimately results in inhibition of cell growth. In a fed-batch process one or more of the nutrients are fed (supplied) to the bioreactor during cultivation to achieve better growth conditions and higher cell densities.

In a continuous system, such as a chemostat, fresh medium is continuously added, while culture liquid is continuously removed to keep the culture volume constant. By changing the rate at which medium is added to the bioreactor, the growth rate of the microorganism cells can be controlled. For cells with a high growth rate such as yeast and bacteria cells, the chemostat typically removes cells from the medium along with the culture liquid in order to maintain a desired cell density.

A perfusion process is a special type of continuous process in which a suspension cell culture is continuously supplied with fresh medium to the bioreactor while spent culture media is continuously harvested. The cells are continuously filtered or otherwise separated from the harvest stream and returned to the bioreactor to maintain a uniform cell density. The constant addition of fresh medium and elimination of waste products provides the cells with the optimal environment to achieve high cell concentrations and thus higher productivity. This allows prolonging healthy cultures, potentially at high cell density, as well as a short residence time of the product in the bioreactor. This is more favourable for product quality and is required for the production of unstable polypeptides. Another advantage of the perfusion mode is that it allows the use of smaller bioreactors compared with fed-batch processes, which provides benefits such as reduced clean-in-place operation and the possibility to use disposable bioreactors instead of stainless steel reactors due to the smaller working volumes. Moreover, product may be continuously harvested by taking out medium (with cells and product) or via a so-called bleed.

Due to an increasing demand for biologically produced medicinal products such a complex polypeptides, including antibodies and other recombinant proteins, perfusion processes are becoming a much more common production platform due to the high productivity in relation to the size of the bioreactor.

As a result of those increasing product quantities, the "bottleneck" in biopharmaceutical production has shifted from upstream production processes toward downstream purification processes. For example, a typical process for downstream processing of monoclonal antibodies involves an affinity purification step (i.e. a capturing step) using a Protein A affinity medium. After the protein A purification step the antibodies are typically further purified by a virus inactivation step followed by other chromatography steps, e.g. bind-elute cation exchange chromatography and/or by bind-elute or flow-through multimodal, mixed mode or anion exchange chromatography and a final nanofiltration purification step.

In such a typical downstream purification process it is commonly the chromatographic capturing step that is presenting significant challenges in terms of facility throughput since, due to the high cost of producing polypeptides including complex monoclonal antibodies the affinity resin is often only saturated until 30-50% of its actual binding capacity during the capturing step to avoid pass through of costly product. In addition the affinity resin in it self is normally also a costly compound. Thus, there is a strong incentive to optimize the utilization of the capturing resin.

For that reason, multicolumn chromatography processes (also called continuous chromatography) has become an object of growing interest. In continuous chromatography, several columns are connected in an arrangement that allows columns to be operated in series and/or in parallel, depending on the method requirements. Thus, all columns can be run in principle simultaneously, but slightly shifted in method steps. The procedure can be repeated, so that each column is loaded, eluted, and regenerated several times in the process. Continuous chromatography (e.g. simulated moving bed (SMB) chromatography) operation may results in a better utilization of chromatography resin, reduced processing time and reduced buffer requirements, all of which benefits process economy. However, SMB chromatography is still not suitable for large scale or cGMP biopharmaceutical production, mainly because it is a complicated method to set up and run, involving the control of a large number of valves and columns.

WO2012074481 discloses a more simple two-column continuous or semi-continuous large-scale chromatographic set up comprising at least two packed bed chromatography columns, at least one tank for holding feed, purification buffers, eluate and pumps and detectors for controlling the operation of the system where each column is loaded, eluted, and regenerated several times in the process. However, WO2012074481 does not disclose a chromatography system also comprising a bioreactor or a process for continuously capturing a biopolymer from a bioreactor harvest stream.

The present invention addresses the need for continuous production and purification of a biopolymer produced in a bioreactor.

SUMMARY OF THE INVENTION

The present invention provides a bioreactor and chromatography system and a method for continuously producing a biopolymer, from a medium containing the biopolymer and waste products, into an elution buffer.

The method employs continuous capturing of the biopolymer onto one or more chromatography units comprising a material having affinity for the biopolymer and, washing and eluting the biopolymer for separating the biopolymer into an elution buffer and optionally reusing the chromatography units. This system provides several advantages, one advantage being that the biopolymer is directly and continuously provided to the capturing columns and not stored in a hold tank thereby resulting in a faster processing time which significantly reduces deleterious effects of product degradation processes taking place when the product is exposed to proteases and glycosidases in the crude cell culture supernatant. Another advantage is that no hold and/or storage container is necessary thereby reducing equipment and making the overall process more efficient.

Moreover, by employing two or more chromatography units operated alone or in series, they can either both be loaded at the same time or each of them can interchangeable be loaded, eluted, and regenerated several times during the purification process. This allows for much more efficient use of the chromatography units in that the biopolymer that is present in a flow-through from the first chromatography unit is captured on the second chromatography unit which allows for complete saturation of the chromatography unit with biopolymer before the biopolymer is washed and eluted from the chromatography unit.

This is illustrated in working example 1 that is directed to chromatography experiments performed in normal mode and in overloaded mode for assessing dynamic binding capacity of protein A chromatography and the quality of the purification step in relation to residual host cell protein and DNA. Overload and normal load chromatography runs were conducted using an agarose based gel (MabSelect SuRe) and a silica based resin (ProVance) resulting in similar yields and purity (see Table 6). However, running the MabSelect SuRe column in overload mode resulted in a product recovery of 65 to 85% higher than running in normal mode. A chromatography run using ProVance in overload mode resulted in an increase in product load capacity of 23%.

Moreover, in a chromatography run where both the load and the column were placed in a thermo cabinet at 35° C. resulted in a 50% reduction in residual DNA contamination and in a 24% reduction in host cell protein. Further advantages will be apparent from the disclosure below.

One aspect of the invention relates to a bioreactor arrangement for producing a biopolymer expressed by a cell, wherein the bioreactor arrangement comprises a bioreactor system and a chromatography system wherein the bioreactor system comprises:
a cell culture vessel (50) for holding a medium comprising the biopolymer and waste products wherein the cell culture vessel (50) comprises a product harvest module (51), wherein the product harvest module (51) has an outlet (16), and
wherein the chromatography system comprises:
a first chromatography unit (2) and a second chromatography unit (3) both comprising material having affinity for the biopolymer, wherein the first chromatography unit (2) has an inlet (12) and an outlet (13) and the second chromatography unit (3) has an inlet (14) and an outlet (15),
wherein the outlet (16) of the product harvest module (51) is in fluid connection with the inlet (12) of the first chromatography unit (2) and in fluid connection with the inlet (14) of the second chromatography unit (3),
wherein a first valve means (31) is located between the outlet (16) of the product harvest module and the inlet (12) of the first chromatography unit (2), and a second valve means (32) is located between the outlet (16) of the product harvest module and the inlet (14) of the second chromatography unit (3),
wherein the outlet (13) of the first chromatography unit (2) is in fluid connection with the inlet (14) of the second chromatography unit (3), and a third valve means (33) is located between the outlet (13) of the first chromatography unit (2) and the inlet (14) of the second chromatography unit (3), and the outlet (15) of the second chromatography unit (3) is in fluid connection with the inlet (12) of the first chromatography unit (2), and a fourth valve means (34) is located between the outlet (15) of the second chromatography unit (3) and the inlet (12) of the first chromatography unit (2).

Another aspect of the invention relates to a method for producing a biopolymer in a bioreactor arrangement, wherein the bioreactor arrangement comprises a bioreactor system and a chromatography system wherein the bioreactor system comprises:
a cell culture vessel (50) for holding a medium comprising the biopolymer and waste products wherein the cell culture vessel (50) comprises a product harvest module (51), wherein the product harvest module (51) has an outlet (16), and
wherein the chromatography system comprises:
a first chromatography unit (2) and a second chromatography unit (3) both comprising material having affinity for the biopolymer, wherein the first chromatography unit (2) has an inlet (12) and an outlet (13) and the second chromatography unit (3) has an inlet (14) and an outlet (15),
wherein the outlet (16) of the product harvest module (51) is in fluid connection with the inlet (12) of the first chromatography unit (2) and in fluid connection with the inlet (14) of the second chromatography unit (3),
wherein a first valve means (31) is located between the outlet (16) of the product harvest module and the inlet (12) of the first chromatography unit (2), and a second valve means (32) is located between the outlet (16) of the product harvest module and the inlet (14) of the second chromatography unit (3),
wherein the outlet (13) of the first chromatography unit (2) is in fluid connection with the inlet (14) of the second chromatography unit (3), and a third valve means (33) is located between the outlet (13) of the first chromatography unit (2) and the inlet (14) of the second chromatography unit (3), and the outlet (15) of the second chromatography unit (3) is in fluid connection with the inlet (12) of the first chromatography unit (2), and a fourth valve means (34) is located between the outlet (15) of the second chromatography unit (3) and the inlet (12) of the first chromatography unit (2),
wherein the method comprises:
(a) fermenting cells expressing the biopolymer in a suitable medium under suitable conditions until a pre-determined level of cells and/or biopolymer is reached in the cell culture vessel (50),
(b) harvesting the biopolymer by removing medium comprising biopolymer and waste products via the product harvest module (51), and
(c) leading the medium comprising the biopolymer and waste products through the fluid connection from the outlet (16) of the product harvest module (51) to the inlet (12) of the first chromatography unit (2) wherein the biopolymer is captured on the first chromatography unit (2), and medium and waste products continues through the outlet (13) of the first chromatography unit (2) until a first pre-determined level of binding capacity is reached in the first chromatography unit (2), wherein the fluid connection from the outlet (16) of the product harvest module (51) to the inlet (14) of the second chromatography unit (3) is closed by the second valve means (32) and wherein the fluid connection from the outlet (13) of the first chromatography unit (2) to the inlet (14) of the second chromatography unit (3) is closed by the third valve means (33), (d) when the first pre-determined level of binding capacity is reached, leading the medium comprising the biopolymer and waste products through the fluid connection from the outlet (13) of the first chromatography unit (2) to the inlet (14) of the second chromatography unit (3) and through the second chromatography unit (3) for a specified setting for the biopolymer un-captured by the first chromatography unit (2) to be captured on the second chromatography unit (3), and medium and waste products continues through the outlet (15) of the second chromatography unit (3), until a second pre-determined level of binding capacity is reached in the first chromatography unit (2) and/or (3), wherein the fluid connection from the outlet (16) of the product harvest module (51) to the inlet (14) of the second chromatography unit (3) is closed by the second valve means (32), (e) when the second pre-determined level of binding capacity is reached, leading the medium comprising the biopolymer and waste products through the fluid connection from the outlet (16) of the product harvest module (51) to the inlet (14) of the second chromatography unit (3) wherein the biopolymer is captured on the second chromatography unit (3), and medium and waste products continues through the outlet (15) of the second chromatography unit (3), until a third pre-determined level of binding capacity is reached in the second chromatography unit (3), wherein the fluid connection from the outlet (16) of the product harvest module (51) to the inlet (12) of the first chromatography unit (2) is closed by the first valve means (31), and wherein the fluid connection from the outlet (15) of the second chromatography unit (3) to the inlet (12) of the first chromatography unit (2) is closed by the fourth valve means (34), wherein during or after step e)

(i) washing the first chromatography unit (2) with a specified concentration of water and buffer by leading wash buffer through the fluid connection from the outlet (21) of the wash buffer container (4) to the inlet (12) of the first chromatography unit (2), through the first chromatography unit (2), and through the outlet (13) of the first chromatography unit (2), until a first pre-determined level of washing is reached, (ii) when the first pre-determined level of washing is reached, eluting the biopolymer from the first chromatography unit (2) by leading elution buffer through the fluid connection from the outlet (22) of the elution buffer container (5) to the inlet (12) of the first chromatography unit (2), through the first chromatography unit (2), and through the outlet (13) of the first chromatography unit (2), until a first pre-determined level of eluating is reached, and collecting the eluate, (f) when the third pre-determined level of binding capacity is reached, leading the medium through the fluid connection from the outlet (15) of the second chromatography unit (3) to the inlet (12) of the first chromatography unit (2) and through the first chromatography unit (2) for a specified setting for the biopolymer un-captured by the second chromatography unit (3) to be captured on the first chromatography unit (2), and medium and waste products continues through the outlet (13) of the first chromatography unit (2) until a fourth pre-determined level of binding capacity is reached in the first and/or second chromatography unit (2) and/or (3), wherein the fluid connection from the outlet (16) of the product harvest module (51) to the inlet (12) of the first chromatography unit (2) is closed by the first valve means (31), (g) when the fourth pre-determined level of binding capacity is reached, leading the medium comprising the biopolymer and waste products through the fluid connection from the outlet (16) of the product harvest module (51) to the inlet (12) of the first chromatography unit (2) wherein the biopolymer is captured on the first chromatography unit (2), and medium and waste products continues through the outlet (13) of the first chromatography unit (2), until a fifth pre-determined level of binding capacity is reached in the first chromatography unit (2), wherein the fluid connection from the outlet (16) of the product harvest module (51) to the inlet (14) of the second chromatography unit (3) is closed by the second valve means (32), wherein during or after step g)

(iii) washing the second chromatography unit (3) with a specified concentration of wash buffer by leading wash buffer through the fluid connection from the outlet (21) of the wash buffer container (4) to the inlet (14) of the second chromatography unit (3), through the second chromatography unit (3), and through the outlet (15) of the second chromatography unit (3), until a second pre-determined level of washing is reached, (iv) when the second pre-determined level of washing is reached, eluting the biopolymer from the second chromatography unit (3) by leading elution buffer through the fluid connection from the outlet (22) of the elution buffer container (5) to the inlet (14) of the second chromatography unit (3), through the second chromatography unit (3), and through the outlet (15) of the second chromatography unit (3), until a second pre-determined level of eluating is reached, and collecting the eluate, (h) optionally, repeating step (c) to (g), and optionally, purifying the biopolymer from the collected eluate(s).

In a further aspect, the invention relates to the use of a chromatography system as described herein for producing a biopolymer from a medium comprising the biopolymer and waste products.

Further objects of the present invention will become apparent in view of the present description, figures, examples and claims.

DETAILED DESCRIPTION OF THE INVENTION

Figure 1:
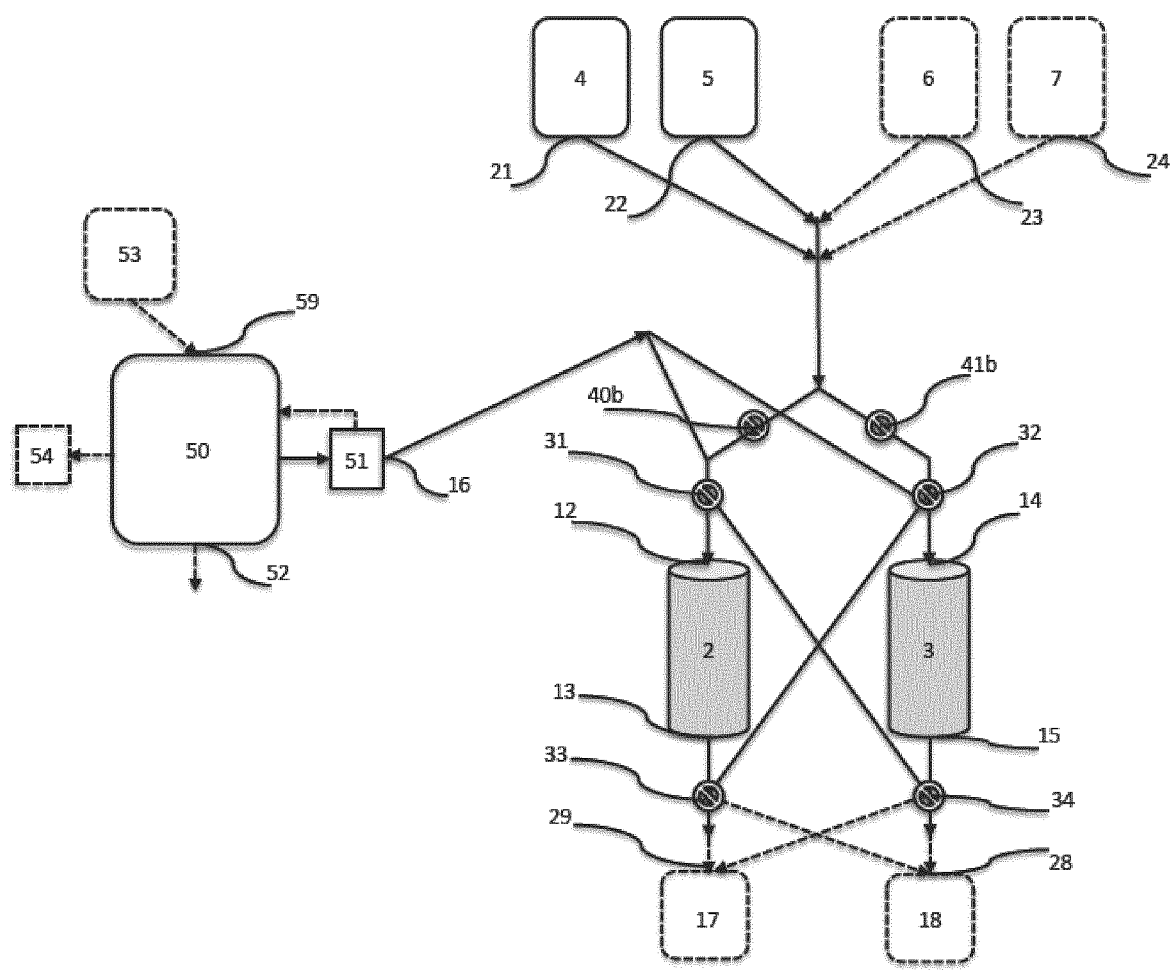
FIG. 1 is a schematic illustration of an bioreactor arrangement system according to the present invention.

The bioreactor arrangement of the present invention comprises a bioreactor system and a chromatography system wherein the bioreactor system includes a cell culture vessel comprising a product harvest module and at least one medium container. Optionally the bioreactor system also includes a water and/or buffer supply, an inline medium dilution system, and a bleed outlet. It may also contain additional components such as an impurity filter unit. The chromatography system includes two chromatography units, a first and a second chromatography unit holding material having affinity for the biopolymer, at least one wash buffer container and at least one elution buffer container, wherein the first and second chromatography units have inlets and outlets that are in fluid connection with each other, the product harvest module and the wash and elution buffer containers. Optionally the chromatography system also includes eluate and waste containers, cleaning buffer and equilibration buffer containers, an inline buffer dilution system and a water and/or buffer supply. The characteristics of the individual components of the system, and their function in the context of the method of the invention for producing a biopolymer will be explained in detail in the following.

Biopolymers

As used herein the term "biopolymer" means a polypeptide, a protein or virus particle, which can be native or biologically or synthetically modified, including fragments, multimers, aggregates, conjugates, fusion products etc. In one embodiment, the biopolymer is a recombinant protein such as an antibody. In another embodiment, the biopolymer is a virus particle or part thereof, for example a protein coat, for use as a vaccine.

In a preferred embodiment of the present invention the product is a polypeptide or protein. As used herein, the terms "protein" or "polypeptide" may be used interchangeably and refer to a chain of amino acids longer than about 30 amino acid residues. Proteins can exist as monomers or multimers, comprising two or more assembled polypeptide chains, fragments of proteins, polypeptides, oligopeptides, or peptides.

Examples of polypeptides of interest that may be produced using the systems and methods of the invention include recombinant therapeutic proteins such as antibodies or fragments thereof, blood clotting factors, cytokines, enzymes, peptide hormones, etc. Specific examples of such proteins include human growth hormone, follicle-stimulating hormone, Factor VIII, Factor VII, Factor IX, erythropoietin (EPO), granulocyte colony-stimulating factor (G-CSF), alpha-galactosidase A, alpha-L-iduronidase (rhIDU; laronidase), N-acetylgalactosamine-4-sulfatase (rhASB; galsulfase), DNAse, tissue plasminogen activator (TPA), glucocerebrosidase, interferons (IF) such as interferon-alpha, interferon-beta and interferon-gamma, insulin, insulin derivatives, insulin-like growth factor 1 (IGF-1), tenecteplase, antihemophilic factor, human coagulation factor, and etanercept; and antibodies such as Trastuzumab, Infliximab, Basiliximab, Belimumab, Daclizumab, Adalimumab, Abciximab, Afutuzumab, Alemtuzumab, Cetuximab, Daclizumab, Denosumab, Eculizumab, Edrecolomab, Golimumab, Ibritumomab tiuxetan, Mepolizumab, Motavizumab, Natalizumab, Ofatumumab, Omalizumab, Oregovomab, Palivizumab, Pemtumomab, Pertuzumab, Ranibizumab, Rituximab, Tefibazumab and Zanolimumab.

In a particular embodiment of the present invention the biopolymer is a polypeptide or protein or a recombinant protein such as an antibody or a fragment thereof, where a fragment can e.g. be a Fab fragment, Fv fragment or single chain Fv (scFv) fragment, a blood clotting factor, a cytokine, an enzyme or a peptide hormone.

Polypeptides are expressed under the control of regulatory sequences called promoter sequences. Cells expressing a polypeptide may be under the control of a constitutive promoter (i.e. unregulated sequences; this allows for continual transcription of the associated gene) or under control of an inducible promoter (regulatory sequences induced by the presence or absence of biotic or abiotic factors). In some cases, if the polypeptide of interest has limited stability or exhibits toxic effects on the host cell, it may be convenient to express it under control of an inducible promoter such that the cells first are grown to a desired cell density, after which expression of the polypeptide is induced by adding an inducer or by changing the temperature and or the pH of medium. An example of a constitutive promoter is a Chinese hamster EF-1α promoter. In one embodiment, the biopolymer is expressed under control of Chinese hamster EF-1α regulatory sequences.

By use of the bioreactor arrangement and method of the invention, it is possible to express polypeptides such as antibodies with high productivity. Thus, in one embodiment, the cells express a polypeptide, e.g. an antibody, and have a productivity of at least 1 gram/L/day, and preferably higher, such as 2 or 3 gram/L/day or more.

Bioreactor System

As used herein the term "bioreactor system" refers to any device or system that supports a biologically active environment, for example for cultivation of cells for production of a biological product. Bioreactors may range in size from a few liters to several cubic meters (i.e. several 1000 liters), and may be a conventional bioreactor based on a culture vessel of e.g. stainless steel or glass or a "single-use" bioreactor based on a disposable material such as a disposable bag.

While bioreactors have in the past typically been of the conventional type, most often based on stainless steel tanks, disposable bioreactors based on a disposable bag, typically made of a multilayer plastic material, are becoming more prevalent. For agitation, some single-use bioreactors use stirrers similar to those of conventional bioreactors, but with stirrers integrated into the plastic bag, while other single-use bioreactors are agitated by means of a rocking motion. Stirred single-use bioreactors may have a volume of up to several thousand liters, e.g. 2000 to 5000 liters, while rocking single-use bioreactors typically have a volume of up to about 1000 liters.

Single-use bioreactors have several advantages compared to conventional bioreactors, including reduced cleaning and sterilization demands, along with significant accompanying cost savings. In addition, complex qualification and validation procedures for pharmaceutical production can be simplified, and there is a reduced risk of cross contamination. Further, since single-use bioreactors contain fewer parts compared with conventional bioreactors, initial and maintenance costs are reduced.

Based on the mode of operation, a bioreactor may be classified as batch, fed-batch or continuous. Examples of continuous bioreactors are a chemostat and a perfusion bioreactor.

In one embodiment, the bioreactor system of the invention is a continuous system, i.e. a perfusion or chemostat bioreactor. Perfusion bioreactors are typically used for cultivation of mammalian cells, while chemostat bioreactors are typically used for cultivation of microorganisms such as bacteria or yeast cells. In a further embodiment the biopolymer is produced by a continuous process e.g. in a chemostat process or in a perfusion process.

The bioreactor is typically equipped with at least one product harvest module (51) attached to the bioreactor, one or more inlets (59) for supplying culture medium to the cells, and with one or more outlets (16) and (52) for harvesting product or emptying the bioreactor. In one embodiment the bioreactor system further comprises at least one medium container (53) in fluid connection with the inlet (59) of the cell culture vessel (50).

As used herein the term "inlet" is intended to encompass any means that enables the introduction of fluid, such as medium, buffer, or water, into a container, tank or unit, and is an opening which is typically equipped with a fitting whereto for instance a tube or a valve can be connected. An inlet of a chromatography unit is for example the end-fitting of a chromatography column to which the fluid connection(s) can be attached.

As used herein the term "outlet" is intended to encompass any means that enables the fluid, such as medium, buffer, or water, to leave a container, tank or unit and is an opening which is typically equipped with a fitting whereto for instance a tube or a valve can be connected. An outlet of a chromatography unit is for example the end-fitting of a chromatography column to which the fluid connection(s) can be attached.

The term "fluid" as used herein is intended to define any substance which flows and therefore includes liquids and gases which are able to flow. As used herein the term "in fluid connection" means that fluid, such as liquid, e.g. medium or buffer, can flow between an inlet of one container, tank or unit and an outlet of another container, tank or unit. The fluid connection may be interrupted by one or more valves and/or holding containers such that the flow of fluid through the fluid connection can be started and stopped whenever decided. Typically, most of the parts of the chromatography system that are in fluid connection have a fluid connection that may be interrupted. For example, if a buffer container is in fluid connection with a chromatography unit this means that a flow of the buffer to the chromatography unit can be realized if decided, but typically there is at least one valve located in the fluid connection between the buffer container and the chromatography unit, such that the fluid flow can be stopped when decided and started when decided.

Typically, the bioreactor's environmental conditions such as gas (i.e., air, oxygen, nitrogen, carbon dioxide) flow rates, temperature, pH and dissolved oxygen levels, and agitation speed/circulation rate can be closely monitored and controlled. In one embodiment, the bioreactor system comprises a water and/or buffer supply (55), and an inline medium dilution system (56). It may also contain additional components such as an impurity filter unit (54).

The bioreactor may optionally also include a separate inlet for adding components such as vitamins or growth factors. In this case, such components may be added to the cell culture vessel in addition to the diluted medium, and may be either in concentrated or diluted form.

Cell Culture Vessel

A "cell culture vessel" as used herein refers to an integral part of a bioreactor system in which cells are grown under suitable conditions in a suitable medium. The cell culture vessel may be a single-use vessel, e.g. a disposable bag, or a conventional reusable vessel, typically a stainless steel or glass vessel, as explained above. Stainless steel vessels are typically configured with predefined port assemblies, whereas single-use bags use pre-sterilized plastic cultivation chambers that are discarded after use. This eliminates space-consuming and expensive clean-in-place (CIP) and steam-in-place (SIP) installations while reducing production turn-around times.

In one embodiment of the present invention the cell culture vessel (50) typically has a volume of at least 50 L, preferably at least 100 L, more preferably at least 250 L, and still more preferably at least 500 L. In many cases, the volume will be still higher, e.g. at least 1000 L or at least 2000 L.

Product Harvest Module

As used herein the term "product harvest module" is intended to encompass any separation device capable of, for example, separating polypeptides from cells, cell debris and impurities larger than the product of interest. The product harvest module may be operated to continuously harvest the product in a harvest stream that is provided for further downstream processing.

The product harvest module may also be a separation device such as a cell retention device that can separate cells from the product harvest stream such that the cells are retained in the cell culture vessel.

There are two major classes of techniques for the separation of cells from the medium, namely by gravitational or centrifugal sedimentation, or by filtration (for example tangential filtration such as alternating tangential-flow filters, e.g. axial rotation filtration or as spin filters, flow filters, vortex filters or cross flow filtration). In one embodiment, the product harvest module (51) is a separation device based on gravitational or centrifugal sedimentation. In a preferred embodiment the product harvest module (51) is a separation device based on alternating tangential-flow filtration.

Gravitational separation is an industrial method of separating two components, either a suspension or a dry granular mixture in which separation of the components by gravity is practical. This method can be used to separate out solids from a liquid mixture if the solids are not soluble in the liquid. The skilled person will know how to attach suitable gravitational separation devices to a bioreactor.

Centrifugal separation is another well-known technique to separate out particles in suspension. Commercially available separators utilizing centrifugal force for separation fall in one of two categories, rotary centrifuges or hydrocyclones. Hydrocyclones are operated by creating a physical vortex within a cylindrical vessel, generating centrifugal force. The heavier phase is forced to the outside portion of the fluid and the lighter fluid stays in the inside as a core. As the fluid continues flowing, the separated portions are directed to different outlets. Suitable centrifugal separation devices are known and commercially available, and use of these together with a bioreactor will be familiar to those skilled in the art.

In another embodiment the product harvest module (51) is a filter unit, in which case the product harvest module may be referred to as a product filter. A product filter is often selected with a pore size in the range of from a nominal molecular weight cut-off (NMWC) of about 50,000 daltons (50 kDa) to about 2 µm, such as from an NMWC of about 100,000 daltons (100 kDa) to a pore size of about 1 µm.

As known to the skilled person, a suitable product filter cut-off will depend on the size of product of interest. In a preferred embodiment, the product filter has an NMWC pore size of at least about 1.5 times the MW of the biopolymer (e.g. polypeptide) of interest. For instance, if the MW of a polypeptide of interest is 100,000 (100 kDa) the preferred cut-off of the product filter will be an NMWC of at least 150,000 (150 kDa). More preferably, the product filter has an NMWC pore size of at least 2 times the MW of the polypeptide of interest.

The skilled person knows how to select filters suitable for acting as product filters. An examples of such a suitable filter is regenerated cellulose lose membranes that exhibit low protein binding, filtration efficiency, exceptional purity, and a broad choice of pore sizes. Regenerated cellulose filter media are hydrophilic and offer broad chemical compatibility. Regenerated cellulose filters are available in many designs including single use filters that are discarded after saturation and replaced with new filters or as multi use that are repeatedly used, cleaned and regenerated.

When the cells present in the bioreactor reach a satisfactory cell density or when there is sufficient product present in the outflow through the harvesting outlet, harvest of the product may be initiated. This may be determined by measuring the cell density, for example using a spectrophotometer, or by measuring the amount of the product of interest by known means, for example using a suitable protein assay method in the case of a polypeptide product.

The bioreactor system may also comprise additional components such as one or more medium container, a further outlet, such as for bleed and a impurity filter unit (54) for removing undesired chemical or biological compounds produced by the cells present in the bioreactor.

Medium Container

As used herein the term "medium container" is intended to encompass any kind of container, e.g. a rigid tank of e.g. steel, glass or plastic or a collapsible and/or disposable bag, that holds cell culture medium and/or nutrients. In the context of the present invention, the medium container is connected to at least one inlet of the cell culture vessel, and the cell culture medium and/or nutrients is provided to the cell culture vessel at a rate according to the need of the cells inside the cell culture vessel.

Typically, the medium and/or nutrients present in the medium container is prepared from more concentrated solutions or powder.

In an embodiment op the present invention the medium container may be connected to at least one inlet end of an inline dilution system, and the cell culture medium and/or nutrients will typically be present in the medium container in a more concentrated form than concentration of the same medium or nutrients when present inside the culture vessel.

In one embodiment of the invention, the bioreactor system may comprise two or more medium containers, each of which is in fluid connection with an inlet of the inline dilution system. The use of two or more medium containers may be advantageous in order to be able to further reduce container size, space requirements, etc., for example by using one container to hold medium components or nutrients having a relatively low solubility and another container to hold other medium components or nutrients that have a higher solubility. By having the low solubility components in a separate container, the volume of the container comprising the other components that have a higher solubility may be reduced. A further advantage of this approach is that components with a low solubility can be stored under conditions that contribute to increasing their solubility, for example by means of suitable pH adjustment. Medium and nutrients from the two or more medium containers can be mixed in suitable amounts via the inline medium dilution system in order to obtain a desired final culture medium composition.

In one embodiment at least one medium container (53) in fluid connection with the inline dilution system (56) has a volume of at least 10 L, such as at least 50 L, such as at least 100 L, e.g. at least 250 L.

In an embodiment, the concentrated medium in the medium container(s) (53) may be kept at a reduced temperature of e.g. 1-10° C., such as about 5° C. In this case, the diluted medium is preferably pre-heated prior to being added to the culture vessel (50). This may be performed by heating the diluted medium as such or by mixing the concentrated medium with water/buffer that has been pre-heated to a desired temperature. For example, the diluted medium may be pre-heated to the same temperature as the temperature of the medium inside the culture vessel.

In a other embodiment the medium from the medium container (53) is mixed with water/buffer from the water/buffer supply (55) that has been pre-heated, or wherein the diluted medium is pre-heated prior to being added to the cell culture vessel.

Bleed Outlet

As used herein the term "bleed outlet" or "outlet for bleed" (used interchangeably) is an outlet from the cell culture vessel that allows medium containing cells, cell debris and impurities to be removed from the cell culture vessel. It may be constructed as a separate outlet, or it may be built together with the product harvest module. Bleeding of cells helps to ensure optimal productivity in continuous fermentation processes, in particular for perfusion processes, as it serves to e.g. improve overall cell culture viability, to avoid accumulation of dead cells and to prevent filter clogging. For cultures operated in perfusion mode it is a common practice to make bleeds daily if the viability of the cells drops to for example below 80% or when the cell density reaches a certain level, for example around 30 million cells/ml. During the bleeds up to 10% of the medium in the cell culture vessel may typically be removed, and this amount may increase with increasing cell density such that the bleeds may be used to regulate the cell density in the cell culture vessel.

While perfusion bioreactors will normally contain a bleed outlet, chemostat bioreactors used for e.g. bacteria or yeast cultivation generally do not include a bleed outlet.

In one embodiment the cell culture vessel (50) comprises a further outlet (52), such as for bleed.

Impurity Filter Unit

Numerous specialized filters and filtration methods have been developed to separate materials according to their chemical and physical properties. Known filters include flat surface filters, pleated filters, multi-unit cassettes, and tubular forms such as hollow fibers. For the invention described herein any system of ultrafiltration technology can be applied as long as sterility can be ensured.

As used herein the terms "impurities", "waste" and "waste products" refers to undesired chemical or biological compounds produced by the cells present in the bioreactor, or which arise from cells that die or break open during the fermentation process. Impurities, waste and waste products are may be used interchangeably and include e.g. ethyl alcohol, butyl alcohol, lactic acid, acetone ethanol, gaseous compounds, peptides, lipids, ammonia, aromatic compounds, and DNA and RNA fragments, as well as media components or brake down products of the biopolymer.

Examples of filtration systems applicable for use in the production of polypeptides and removal of impurities as described herein are systems such as cartridge systems, plate and frame systems, and hollow fiber systems. The systems can be operated by pumping liquid over the membrane, by vibration (e.g. as supplied by PallSep™) or by alternating tangential flow (ATF), and both polymeric and ceramic membranes are well suited for the filtration process. A skilled person will be able to select a membrane with suitable properties.

Hollow fiber membranes have been successfully employed in a wide variety of industries, and have several benefits that include high membrane packing densities the ability to withstand permeate back-pressure, thus allowing flexibility in system design and operation. Hollow fiber cartridges can operate from the inside to the outside during filtration, allowing process fluid (retentate) to flow through the center of the hollow fiber and permeate to pass through the fiber wall to the outside of the membrane fiber. Tangential flow can help limit membrane fouling. Other operating techniques that can be employed with hollow fiber membrane systems include back flushing with permeate and retentate reverse flow.

Accordingly, the impurity filter (54) may be located in an external filter module attached to the bioreactor. Alternatively, the impurity filter may be located inside the bioreactor. The filter unit can also contain pumps or systems for preventing fouling of the filter such as an ATF system or the PallSep™ system in which controlled horizontal oscillation moves the membrane elements through the feed fluid. The oscillation generates vibrational energy at the membrane surface, giving shear (higher than that typically generated in conventional tangential flow filtration systems) that is limited to a small boundary layer above the membrane surface, and which is not applied to the bulk of the fluid. This ensures that even in high solids feed streams, the membranes do not block with the retained species.

The system can, depending on the metabolites to be removed and the product in question, be equipped with membranes with a molecular weight cut-off value from a few hundred to tens of thousands. Often membranes with a cut-off between 1000 and 20,000 (1-20 kDa) are used. The benefit of using a membrane with a cut-off of about 10,000 (10 kDa) or below, preferably around 5000 (5 kDa), is that growth factors such as insulin and IGF-1 will be retained in the bioreactor.

During an extended run, it is possible to change the filters and re-sterilize the system, or if using disposable filters simply exchange it with a new one, without terminating the fermentation.

The skilled person will be able to select a suitable filter type for removal of impurities and a suitable membrane nominal molecular weight cutoff (NMWC) pore size with respect to allowing impurities to perfuse out of the impurity filter and harvest the polypeptide of interest through the product harvesting outlet.

In one embodiment, the impurity filter unit is selected from a membrane filter, a gravitational separation unit and a centrifugal separation unit.

The impurity filter is often selected with an NMWC within the range of 1000 to 30,000 (1 30 kDa), such as in the range of 2000 to 20,000 (2-20 kDa) or in the range of 2000 to 15,000 (2-15 kDa). However, if the product is a cell an impurity filter may be selected with an NMWC in the range of 1000 to 500,000 (1-500 kDa), but normally it is preferred that the impurity filter has a cut-off of less than 20,000 (20 kDa). Thus, in one embodiment the impurity filter unit is a membrane filter having an NMWC pore size of at least 1000, such as within the range of 2000 to 15,000.

In a preferred embodiment the impurity filter unit is a membrane filter having a molecular weight cut-off (NMWC) pore size of a maximum of 80% of the molecular weight (MW) of the product (e.g. polypeptide) of interest. For instance if the MW of the polypeptide of interest is 100,000 (100 kDa) the preferred maximum cut-off of the impurity filter will in this case be 80,000 (80 kDa). More preferably, the impurity filter has an NMWC pore size of a maximum of 50% of the MW of the polypeptide of interest. Thus, in one embodiment the impurity filter has a molecular weight cut-off (NMWC) pore size of a maximum of 80% of the MW of the biopolymer, such as a maximum of 50%.

In a still further embodiment the cell culture vessel (50) further comprises an impurity filter unit (54) in fluid connection with the cell culture vessel (50).

Chromatography System

As used herein the term "chromatography system" refers to any device or system for capturing a biopolymer from a medium comprising the biopolymer and waste products.

The chromatography system of the present invention includes two or more chromatography units that allows for capturing the biopolymer and thereby separating the biopolymer from the medium and the waste products. As used herein the term "chromatography unit" refers to a separate chromatography device, such as a column or a filter unit that may hold any kind of material having higher affinity for the biopolymer than for the waste products, thereby allowing for its separation.

As used herein the term "affinity" refers to the selective adsorption of the biopolymer onto an affinity ligand. The affinity ligand can bind to a defined site on the biopolymer and may be attached to an inert chromatographic support. The affinity ligand can also interact with the biopolymer through ionic interactions. When the medium containing the biopolymer passes through the chromatographic support, the biopolymer binds to the solid support via interaction of the binding site, or through ionic interactions, with the immobilized ligand. The specifically bound biopolymer can then be recovered by changing the environmental conditions (pH, ionic strength, solvents) to weaken the binding interaction. In other cases the bound biopolymer can then be recovered by addition of calcium and/or Ethylenediaminetetraacetic acid (EDTA) or by increasing their concentration in the elution buffer.

In one embodiment of the present invention the chromatography system can consist of 3 and 4 or more chromatography units. However, such system is a very complex system to control and also demands more space. Using only two chromatography units creates a more simple system which have the advantages easy operation and handling. In a preferred embodiment of the present invention the chromatography system consist of one first chromatography unit (2) and one second chromatography unit (3).

A typical process for downstream processing of monoclonal antibodies involves an affinity purification step (i.e. a capturing step) using a Protein A affinity medium. After the protein A purification step the antibodies are typically further purified by a virus inactivation step followed by other chromatography steps, e.g. bind-elute cation exchange chromatography and/or by bind-elute or flow-through multimodal or anion exchange chromatography and a final nanofiltration purification step. The chromatography system of the present invention may either operate as part of such a purification process or it may operate as an independent unit and contain additional components such as containers for holding waste and eluate.

The ligand that binds to a defined site on the target biopolymer may be attached to an inert chromatographic support. The ligand can also interact with the biopolymer through ionic interactions. When the medium containing the biopolymer passes through the chromatographic support, the biopolymer binds to the solid support via interaction of the binding site, or through ionic interactions, with the immobilized ligand. The specifically bound biopolymer can then be recovered by changing the environmental conditions (pH, ionic strength, solvents) to weaken the binding interaction.

One advantage of this type of chromatography system is the reduced number of steps required for attaining the desired biopolymer purity. The first and second chromatography units may be chromatography columns adapted to be packed with a particulate chromatography resin such as a packed bed chromatography column. It can be an axial or radial column and may comprise a column tube, an inlet porous bed support and an outlet porous bed support, an inlet fluid distributor and an outlet fluid distributor. When packed with the chromatography resin, the resin bed can fill essentially the entire volume between the inlet and outlet porous bed supports. Packed bed chromatography columns may be packed with a resin having affinity towards the biopolymer such as a proteinaceous ligand. The proteinaceous ligand may be derived from Protein A, Protein G, Protein L or an antibody. It can be either a native or recombinant protein A, G, L or antibody or it can be a mutant, fragment or multimer of any of these proteins such as alkali-tolerant recombinant protein A ligand, such as a MABSELECT SURE® or a ProVance® ligand. Such ligands can have very high selectivity and are hence suited for capture of valuable biopharmaceuticals from complex feeds.

In some embodiments the first and second chromatography units may also be based on microporous membrane absorbers as stationary support having the affinity ligands coupled to an activated membrane a hydrogel such as NATRIX®. In general, there are three types of membrane modules used for protein separation: flat sheet, hollow fiber and radial flow. Preferred membrane materials for bioseparations are cellulose, polyamide, polyethylene and polyethersulfone. For membrane chromatography there are some commercially available membranes containing reactive groups, ready for ligand attachment. Sartobind Epoxy®, conceived by Sartorius (Germany), is a regenerated cellulose membrane with nominal pore size of 0.45 µm possessing epoxy groups for the coupling of ligands containing —OH, —NH$_2$ or —SH groups. Another example is Ultrabind® US450 (Pall Corp., USA), which is a polysulfone membrane with 0.45 µm pore size containing aldehyde groups.

In a further embodiment of the present invention the material having affinity for the biopolymer is a rigid, high-flow matrix and alkali-tolerant recombinant protein A ligand, such as a MABSELECT SURE® or a ProVance® ligand.

Optionally, the chromatography system also includes one or more waste container(s), one or more eluate container(s) for collecting the biopolymer, one or more washing buffer container(s), one or more elution buffer container(s), one or more cleaning buffer container(s), one or more equilibration buffer container(s), a water and/or buffer supply and an inline buffer dilution system.

Other components of the chromatography system are means for leading fluid, and valve means for directing the fluid from for example the wash buffer container (4) to the first and/or second chromatography units (2) and/or (3) while blocking for the flow of buffer from the elution buffer container.

As used herein the term "means for leading the medium" is intended to encompass any means that can convey a medium comprising a biopolymer and waste products or a buffer from a container or the inline buffer dilution system through a pipe, tube or connection line to for example a chromatography unit, a waste container, an elution buffer container or to the inline buffer dilution system. Such means could be mediated by gravity or hydraulic force, but typically, it will be a pump.

As used herein the term "a valve means" is intended to encompass any device by which the flow of fluid through a passageway, such as a connection line, may be blocked, permitted, or otherwise regulated by a movable part that shuts, opens, or partially obstructs, respectively, the fluid flow, including but not limited to 2-, 3- or 4-way valves. A valve means is one valve or is more valves, as may be desired, for instance the first valve means (31) between outlet (16) of the product harvest module (51) and the inlet (12) of the first chromatography unit (2) may constitute one valve or may be 2, 3, or 4 valves as desired. Valves can be manually, magnetically, electrically, pneumatically or hydraulically operated if using flexible tubing pinch valves are particularly suitable.

In one embodiment the chromatography system further comprises a waste container (17) having an inlet (29) wherein the waste container (17) is in fluid connection with the outlet (13) of the first chromatography unit (2), wherein the third valve means (33) is located between the outlet (13) of the first chromatography unit (2) and the inlet (29) of the waste container (17). In an other embodiment the chromatography system further comprises a waste container (17) having an inlet (29) wherein the waste container (17) is in fluid connection with the outlet (15) of the second chromatography unit (3), wherein the fourth valve means (34) is located between the outlet (15) of the second chromatography unit (3) and the inlet (29) of the waste container (17). In a still further embodiment of the present invention the inlet (29) of the waste container (17) is in fluid connection with the outlet (13) of the first chromatography unit (2) and in fluid connection with the outlet (15) of the second chromatography unit (3). An advantages of this is, that the waste can be saved and re-purified if significant amounts of biopolymer may be present in the waste fraction.

According to the present invention the eluate may be directly provided to additional chromatography and/or filtration systems for further purification in, which case no eluate container is necessary. The eluate may also be collected and used as it is, or it may be stored for further purification of the biopolymer.

In one embodiment the chromatography system further comprises an eluate container (18) having an inlet (28) wherein the eluate container (18) is in fluid connection with the outlet (13) of the first chromatography unit (2), wherein the third valve means (33) is located between the outlet (13) of the first chromatography unit (2) and the inlet. In another embodiment the chromatography system further comprises an eluate container (18) having an inlet (28) wherein the eluate container (18) is in fluid connection with the outlet (15) of the second chromatography unit (3), wherein the fourth valve means (34) is located between the outlet (15) of the second chromatography unit (3) and the inlet (28) of the eluate container (18). In a further embodiment of the present invention the inlet (28) of the eluate container (18) is in fluid connection with the outlet (13) of the first chromatography unit (2) and in fluid connection with the outlet (15) of the second chromatography unit (3).

Additional components of the chromatography system are containers holding wash buffer, elution buffer and optionally also cleaning buffer and equilibration buffer for washing, eluting, cleaning and equilibrating the first and second chromatography units.

The term "wash buffer container", "elution buffer container", "cleaning buffer container" and "equilibration buffer container" as used herein refers to any kind of container, e.g. a rigid tank of e.g. steel, glass or plastic or a collapsible and/or disposable bag, that holds a wash buffer, an elution buffer, a cleaning buffer and an equilibration buffer, respectively.

In one embodiment the one or more washing, elution, cleaning and equilibration buffer containers may hold ready to use buffer solutions also called "working solution ready buffer" such as for example "working solution ready elution buffer".

Further additional components of the chromatography system are pumps for leading the fluid, medium and/or buffers through the system.

As used herein the term "a pump" is intended to encompass any pumping device suitable for conveying a fluid, e.g. a liquid. Typically, it may either be a separate pumping device or an individual channel in a multichannel pumping device, such as e.g. a multichannel peristaltic pump. Examples of pumps include membrane pumps, hose pumps/peristaltic pumps, valve-less pumps and diaphragm pumps.

Further additional components of the chromatography system are degassers, debubblers and/or bubble traps devices as well as detectors for monitoring the operation of the system, including the flow of medium and/or buffers.

During complex operation of liquids, bubbles may form and affect the flow of the liquid through the connection lines and/or through the first and second chromatography units. Bubbles caught in the chromatography units may be especially problematic for maintaining correct flow through the system. Thus, degassers, debubblers and/or bubble traps devices may for example be located before or after the inline buffer dilution system or before the first and/or second chromatography unit (2) and/or (3). The skilled person knows how to elect the most suitable degassers, debubblers and/or bubble traps devices and where to locate them in the chromatography system.

In one embodiment of the present invention the chromatography system comprises a bubble trap located before the inlet (12) of the first chromatography unit (2) and/or a bubble trap located before the inlet (14) of the second chromatography unit (3). In another embodiment of the present invention the chromatography system comprises a bubble trap located before the inlet (26a) or (26b) of the inline buffer dilution system (9).

Detectors suitable for monitoring the concentration of the biopolymer or the waste products can be connected to the outlets of the first chromatography unit (2) and/or the second chromatography unit (3). Typical, detectors include single or multi-wavelength UV monitors, refractive index detectors, light scattering detectors flow detectors, mass detectors and near-infrared (NIR) sensors. The skilled person knows how to elect the most suitable detector depending on the affinity material in the chromatography units and the biopolymer. In one embodiment of the present invention a detector suitable for monitoring the concentration of the biopolymer, such as a UV absorption detector, a refractive index detector or a light scattering detector is connected to the outlet (13) of the first chromatography unit (2) and/or to the outlet (15) of the second chromatography unit (3).

Detectors suitable for monitoring the flow rates or pressure to and from the inline buffer dilution system can be connected to the inlets (26a) and (26b) and/or to the outlet (27) of the inline buffer dilution system (9). Detector(s) for monitoring the blend quality from the inline dilution e.g. pH conductivity of the blended solutions can be connected to the outlet (27) of the inline buffer dilution system (9).

In one embodiment of the present invention the chromatography system comprises a detector suitable for monitoring the concentration of a biopolymer and/or for measuring conductivity or pH of the blended solution. In another embodiment of the present invention the chromatography system comprises a detector suitable for monitoring the concentration of the biopolymer, such as single or multi-wavelength UV monitors, refractive index detectors, light scattering detectors flow detectors, mass detectors and near-infrared (NIR) sensors. A programmable logic controller may integrate the operation and control of all components in the system.

Pumps may either be a separate pumping device or an individual channel in a multichannel pumping device, such as e.g. a multichannel peristaltic pump. Peristaltic pumps are convenient to use in disposable bioprocessing systems as they do not add any fluid-contact surfaces and they are well adapted for leading of fluids in parallel in that one pump head can be used with several tubes. It is possible to use only one multichannel pump for the entire chromatography system, but it is also possible to use several multichannel pumps. If different flow rates are to be used in different connection lines, it is possible to use tubing of different diameters in the channels of a multichannel peristaltic pump. Further, it is possible to stop the flow in a separate line by releasing the compression of the tubing on the rollers of the pump.

Pumps can be connected to the product harvest module (51), wash buffer (4), elution buffer (5), cleaning buffer (6) or equilibration buffer container (7) or to the outlet of the water supply (8). Pumps can also be connected to inlets or outlets of the inline buffer dilution system (9), the inline medium dilution system (56) or to inlets or outlets of the first chromatography unit (2) or the second chromatography unit (3). The skilled person knows how to elect and place suitable pumps for leading the medium to the cell culture vessel and buffers to the chromatography units.

In one embodiment of the present invention the chromatography system comprises a means for leading the medium comprising biopolymer and waste, such as a pump. In another embodiment of the present invention the chromatography system further comprise a means for leading the wash buffer, a means for leading the elution buffer, a means for leading the cleaning buffer, a means for leading the equilibration buffer, a means for leading the water, and a means for leading the diluted buffer, such as a pump. In a further embodiment of the present invention a pump is located between the outlets (21), (22), (23), (24) and (25) and the inlet (26a) and/or (26b) of the inline buffer dilution system. In a still further embodiment of the present invention a pump is located between the outlet (16) of the product harvest module (51) and the inlets (12) and/or (14) of the chromatography units (2) and (3).

In one embodiment of the present invention the chromatography system further comprises, a wash buffer container (4), having an outlet (21),
an elution buffer container (5), having an outlet (22),
optionally a cleaning buffer container (6), having an outlet (23)
optionally an equilibration buffer container (7), having an outlet (24),
wherein the outlet (21) of the wash buffer container (4) is in fluid connection with the inlet (12) of the of the first chromatography unit (2) and wherein a twelfth valve means (40b) is located between the outlet (21) of the wash buffer container (4) and the inlet (12) of the of the first chromatography unit (2), wherein the outlet (21) of the wash buffer container (4) is in fluid connection with the inlet (14) of the second chromatography unit (3) and wherein a thirteenth valve means (41b) is located between the outlet (21) of the wash buffer container (4) and the inlet (14) of the second chromatography unit (3),
wherein the outlet (22) of the elution buffer container (5) is in fluid connection with the inlet (12) of the of the first chromatography unit (2) and wherein a twelfth valve means (40b) is located between the outlet (21) of the elution buffer container (5) and the inlet (12) of the of the first chromatography unit (2), wherein the outlet (22) of the elution buffer container (5) is in fluid connection with the inlet (14) of the second chromatography unit (3) and wherein a thirteenth valve means (41b) is located between the outlet (22) of the elution buffer container (5) and the inlet (14) of the second chromatography unit (3), optionally, wherein the outlet (23) of the cleaning buffer container (6) is in fluid connection with the inlet (12) of the of the first chromatography unit (2) and wherein a twelfth valve means (40b) is located between the outlet (23) of the cleaning buffer container (6) and the inlet (12) of the of the first chromatography unit (2), wherein the outlet (23) of the cleaning buffer container (6) is in fluid connection with the inlet (14) of the second chromatography unit (3) and wherein a thirteenth valve means (41b) is located between the outlet (23) of the cleaning buffer container (6) and the inlet (14) of the second chromatography unit (3), optionally, wherein the outlet (24) of the equilibration buffer container (7) is in fluid connection with the inlet (12) of the of the first chromatography unit (2) and wherein a twelfth valve means (40b) is located between the outlet (24) of the equilibration buffer container (7) and the inlet (12) of the of the first chromatography unit (2), wherein the outlet (24) of the equilibration buffer container (7) is in fluid connection with the inlet (14) of the second chromatography unit (3) and wherein a thirteenth valve means (41b) is located between the outlet (24) of the equilibration buffer container (7) and the inlet (14) of the second chromatography unit (3).

Inline Dilution

Inline dilution refers to a system of mixing a concentrated solution and water (or some other diluent, e.g. an aqueous buffer) inside a processing line to produce a normal strength, process-ready solution. Inline dilution systems (sometimes called "on-site blending systems") also provide many advantages over purchasing pre-mixed and diluted cell culture media and/or washing, elution, cleaning and equilibration buffers. By using a blending system, a single container of medium or buffer concentrate produces many times its volume in diluted solution. Thus, a single volume of concentrated solution, used to produce the equivalent of many volumes of dilute medium or buffer via the dilution system, greatly reduces facility costs associated with fabrication of large tanks, reduces floor space requirements, and reduces validation and quality control costs as well as spoilage and disposal costs of non-compliant, out-of-date or unused blended solutions. Costs associated with medium and buffer delivery and handling are also greatly reduced. In addition, onsite dilution and mixing increases the variety of medium and buffer concentrations and mixtures that are immediately available, without requiring a corresponding increase in the number of different types of buffer, media and nutrient supplements that must be purchased, thereby reducing facility and operating costs and providing the logistical and administrative advantage of reduced inventory.

Another advantage of inline medium dilution is that if, for example, one component of a medium is consumed at a faster rate at a high cell density than at a low cell density, the medium can be compensated for this by mixing in a higher concentration of this component.

As used herein the term "inline medium dilution system" is the blending systems that provides diluted medium to the culture vessel and the "inline buffer dilution system" is the blending systems that provides diluted buffer washing, elution, cleaning and equilibration buffer solutions to the first and second chromatography units. In one embodiment the inline medium dilution system and the inline buffer dilution system may be build into a single blending system that both provides diluted medium to the culture vessel and diluted buffer washing, elution, cleaning and equilibration buffer solutions to the first and second chromatography units (2) and/or (3).

Inline dilution of concentrated washing, elution, cleaning, equilibration buffer solutions (also just called buffer solutions), medium or nutrient solutions with water or buffer must be made within tight specification ranges for pH, conductivity, osmolality, and temperature, which are critical process parameters. This requires that a precise mixture of the concentrated solution and water can be delivered with minimal deviation over time. Also, the solution must be well mixed prior to delivery to the cell culture vessel.

An inline dilution system may, in its most basic form, be a simple system of tubes or pipes from which concentrated solutions and water/buffer, respectively, are supplied, and that connect with each other at one end before being led into the inlet of the cell culture vessel or provided to a chromatography unit. It may also be a static mixer or a dynamic mixer. There exist several types of static mixers such as so called plate-type mixers or mixers wherein the mixing elements are contained in a cylindrical (tube) or squared housing. In the plate type design mixing is accomplished through intense turbulence in the flow. The housed-elements mixer's fixed can simultaneously produce patterns of flow division and radial mixing. However, more typically the inline dilution system will be a more advanced automated system that allows two or more liquid streams to be brought together in a controlled fashion to meet a target diluted solution concentration. Inline dilution systems are commercially available from different suppliers such as from Novasep, GE Healthcare or for example the system IBD™ 1K Inline Buffer Dilution System from Asahi Kasei Bioprocess (disclosed in U.S. Pat. No. 8,271,139). Such systems are capable of making multi-component blends of up to 20× concentrates and produce a ready-to-use solution offering total blend flow rates of more than 1000 L/h.

In another embodiment the one or more washing, elution cleaning and equilibration buffer containers may hold concentrated buffer solutions that have to be diluted by the inline buffer dilution system with water and/or buffer from the water and/or buffer supply before they are provided to the first and second chromatography units. In a further embodiment at least one of the wash, elution, cleaning or equilibration buffer containers has a volume of at least 10 L, such as at least 50 L, such as at least 100 L, e.g. at least 250 L.

As used herein, the terms "water and/or buffer supply" and "water/buffer supply", are intended to encompass any supply of water or buffer for use in diluting the concentrated medium and nutrients intended for the cell culture vessel and for diluting the concentrated washing, eluating cleaning and equilibration buffer solutions intended for the chromatography units. This can include containers that hold water or a pre-mixed buffer solution for mixing with the concentrated medium or buffer solutions as well as e.g. dilution systems in which a concentrated buffer is mixed with water prior to use in the inline medium dilution system.

As used herein, the term "water supply" is intended to encompass any supply of water, such as a tank, a container, or a tube, holding or leading water for use in diluting the concentrated medium, nutrients, wash buffer, elution buffer, cleaning buffer or equilibration buffer. This can include any supply of suitable water, such as pure water, high-purity water (HPW) or water for injection (WFI) whether stored in a tank or other container or supplied as needed in purified form using e.g. ultrafiltration or reverse osmosis. Due to problems measuring the pH of high-purity water, the water from the water supply may be buffered, with for example, an acid, a base or a salt.

In one embodiment the of the present invention the bioreactor system further comprises a water and/or buffer supply (55) in fluid connection with the cell culture vessel (50). In a further embodiment the bioreactor system further comprises an inline medium dilution system (56) for diluting concentrated medium from the medium container (53), the inline medium dilution system having an inlet (57) and an outlet (58), wherein the inlet (57) is in fluid connection with the medium container (53) and the inlet (57) is in fluid connection with the water/buffer supply (55), and wherein the outlet (58) of the inline medium dilution system (56) is in fluid connection with the cell culture vessel (50).

In an embodiment of the present invention the water and/or buffer supply (55) and the water and/or buffer supply (8) is the same water and/or buffer supply that provides water and/or buffer both to the inline medium dilution system and to the inline buffer dilution system. In an other embodiment the water and/or buffer supply (8) and (55) are independent water and/or buffer supplies where first water and/or buffer supply (55) provides water and/or buffer to the inline medium dilution system and the water and/or buffer supply (8) provides water and/or buffer to the inline buffer dilution system.

In another embodiment the chromatography system further comprises,
a wash buffer container (4), having an outlet (21),
an elution buffer container (5), having an outlet (22),
optionally a cleaning buffer container (6), having an outlet (23)
optionally an equilibration buffer container (7), having an outlet (24),
a water supply (8), having an outlet (25) and an inline buffer dilution system (9) having an inlet (26a) and an outlet (27), wherein the outlet (21) of the wash buffer container (4) is in fluid connection with the inlet (26a) of the inline buffer dilution system (9) and wherein a fifth valve means (35) is located between the outlet (21) of the wash buffer container (4) and the inlet (26a) of the inline buffer dilution system (9), wherein the outlet (22) of the elution buffer container (5) is in fluid connection with the inlet (26a) of the inline buffer dilution system (9) and wherein a sixth valve means (36) is located between the outlet (22) of the elution buffer container (5) and the inlet (26a) of the inline buffer dilution system (9),
optionally, wherein the outlet (23) of the cleaning buffer container (6) is in fluid connection with the inlet (26a) of the inline buffer dilution system (9) and wherein a seventh valve means (37) is located between the outlet (23) of the cleaning buffer container (6) and the inlet (26a) of the inline buffer dilution system (9),
optionally, wherein the outlet (24) of the equilibration buffer container (7) is in fluid connection with the inlet (26a) of the inline buffer dilution system (9) and wherein an eighth valve means (38) is located between the outlet (24) of the equilibration buffer container (7) and the inlet (26a) of the inline buffer dilution system (9),
wherein the outlet (25) of the water supply (8) is in fluid connection with the inlet (26a) of the inline buffer dilution system (9) or is in fluid connection with a separate inlet (26b) of the inline buffer dilution system (9) and wherein a ninth valve means (39) is located between the outlet (25) of the water supply (8) and the inlet (26a) or the separate inlet (26b) of the inline buffer dilution system (9); and wherein the outlet (27) of the inline buffer dilution system (9) is in fluid connection with the inlet (12) of the first chromatography unit (2) and in fluid connection with the inlet (14) of the second chromatography unit (3), wherein a tenth valve means (40) is located between the outlet (27) of the inline buffer dilution system (9) and the inlet (12) of the first chromatography unit (2), and an eleventh valve means (41) is located between the outlet (27) of the inline buffer dilution system (9) and inlet (14) of the second chromatography unit (3).

In one embodiment of the present invention, the inline medium dilution system (56) has a total blend flow rate of at least 0.01 L/min, such as at least 0.1 L/min, such as at least 0.2 L/min, such as at least 0.5 L/min, such as at least 1 L/min, such as at least 2 L/min, such as at least 5 L/min, such as at least 10 L/min. In a further embodiment the inline buffer dilution system (9) has a total blend flow rate of at least 0.01 L/min, such as at least 0.1 L/min, such as at least 0.2 L/min, such as at least 0.5 L/min, such as at least 1 L/min, such as at least 2 L/min, such as at least 5 L/min, such as at least 10 L/min.

In a further embodiment the bioreactor arrangement for producing a biopolymer expressed by a cell, wherein the bioreactor arrangement comprises a bioreactor system and a chromatography system wherein the bioreactor system comprises:
a cell culture vessel (50) for holding a medium comprising the biopolymer and waste products wherein the cell culture vessel (50) comprises a product harvest module (51), having an outlet (16), further outlet (52), such as for bleed and a medium container (53) in fluid connection with the cell culture vessel (50), an impurity filter unit (54) in fluid connection with the cell culture vessel (50), a water and/or buffer supply (55) in fluid connection with the cell culture vessel (50) and an inline medium dilution system (56) for diluting concentrated medium from the medium container (53), the inline medium dilution system having an inlet (57) and an outlet (58), wherein the inlet (57) is in fluid connection with the medium container (53) and the inlet (57) is in fluid connection with the water/buffer supply (55), and wherein the outlet (58) of the inline medium dilution system (56) is in fluid connection with the cell culture vessel (50), and wherein the chromatography system comprises:
a first chromatography unit (2) and a second chromatography unit (3) both comprising material having affinity for the biopolymer, wherein the first chromatography unit (2) has an inlet (12) and an outlet (13) and the second chromatography unit (3) has an inlet (14) and an outlet (15),
a wash buffer container (4), having an outlet (21),
an elution buffer container (5), having an outlet (22),
optionally a cleaning buffer container (6), having an outlet (23)
optionally an equilibration buffer container (7), having an outlet (24),
a water supply (8), having an outlet (25) and an inline buffer dilution system (9) having an inlet (26a) and an outlet (27), wherein the outlet (16) of the product harvest module (51) is in fluid connection with the inlet (12) of the first chromatography unit (2) and in fluid connection with the inlet (14) of the second chromatography unit (3),
wherein a first valve means (31) is located between the outlet (16) of the product harvest module and the inlet (12) of the first chromatography unit (2), and a second valve means (32) is located between the outlet (16) of the product harvest module and the inlet (14) of the second chromatography unit (3), wherein the outlet (13) of the first chromatography unit (2) is in fluid connection with the inlet (14) of the second chromatography unit (3), and a third valve means (33) is located between the outlet (13) of the first chromatography unit (2) and the inlet (14) of the second chromatography unit (3), and the outlet (15) of the second chromatography unit (3) is in fluid connection with the inlet (12) of the first chromatography unit (2), and a fourth valve means (34) is located between the outlet (15) of the second chromatography unit (3) and the inlet (12) of the first chromatography unit (2), and wherein the outlet (21) of the wash buffer container (4) is in fluid connection with the inlet (26a) of the inline buffer dilution system (9) and wherein a fifth valve means (35) is located between the outlet (21) of the wash buffer container (4) and the inlet (26a) of the inline buffer dilution system (9), wherein the outlet (22) of the elution buffer container (5) is in fluid connection with the inlet (26a) of the inline buffer dilution system (9) and wherein a sixth valve means (36) is located between the outlet (22) of the elution buffer container (5) and the inlet (26a) of the inline buffer dilution system (9), optionally, wherein the outlet (23) of the cleaning buffer container (6) is in fluid connection with the inlet (26a) of the inline buffer dilution system (9) and wherein a seventh valve means (37) is located between the outlet (23) of the cleaning buffer container (6) and the inlet (26a) of the inline buffer dilution system (9), optionally, wherein the outlet (24) of the equilibration buffer container (7) is in fluid connection with the inlet (26a) of the inline buffer dilution system (9) and wherein an eighth valve means (38) is located between the outlet (24) of the equilibration buffer container (7) and the inlet (26a) of the inline buffer dilution system (9), wherein the outlet (25) of the water supply (8) is in fluid connection with the inlet (26a) of the inline buffer dilution system (9) or is in fluid connection with a separate inlet (26b) of the inline buffer dilution system (9) and wherein a ninth valve means (39) is located between the outlet (25) of the water supply (8) and the inlet (26a) or the separate inlet (26b) of the inline buffer dilution system (9); and wherein the outlet (27) of the inline buffer dilution system (9) is in fluid connection with the inlet (12) of the first chromatography unit (2) and in fluid connection with the inlet (14) of the second chromatography unit (3), wherein a tenth valve means (40) is located between the outlet (27) of the inline buffer dilution system (9) and the inlet (12) of the first chromatography unit (2), and an eleventh valve means (41) is located between the outlet (27) of the inline buffer dilution system (9) and inlet (14) of the second chromatography unit (3).

There are several approaches for operating the blend procedure. For example, some systems blend the solutions based on conductivity and/or pH data provided by conductivity and pH process analyzers, whereas other systems use volumetric flow rate as the primary means of control, since inline pH and conductivity meters have an inherent tendency to drift and improper calibration may result in false readings.

The inline medium dilution system may be constructed such that all the media components and nutrients are pre-mixed into a single concentrated solution designed to be diluted with water or buffer by e.g. a factor of 1.5 or more, typically two or more, for example a factor of three, a factor of four or a factor of five, or even higher, such as factor of eight or ten, in the inline medium dilution system and subsequently provided to the cell culture vessel. In this case, the system will use a single medium container.

Alternatively, the inline medium dilution system may employ two or more medium containers, e.g. containing different medium components with different solubilities as discussed above. In this case, the system may be constructed such that different media components and nutrients having different concentrations are led into a single mixing chamber by different inlets at different flow rates and diluted in the mixing chamber with water or buffer to the desired concentration (e.g. to the concentration of the medium in the cell culture vessel), where after the diluted mixture is provided to the cell culture vessel. Another option in the case of multiple medium containers is for each medium container to be connected to a separate mixing chamber for dilution with water or buffer. The separate mixing chambers can be further connected to a common mixing chamber, wherein diluted medium from two or more individual separate mixing chambers is mixed together before being led into the culture vessel via a single inlet, or alternatively, diluted medium from individual separate mixing chambers may be led into the culture vessel by way of multiple inlets, e.g. one inlet for each mixing chamber.

In one embodiment the concentrated medium in the medium container (53) is diluted at least by a factor of two with water or buffer from the water/buffer supply (55) before being fed to the culture vessel (50), e.g. by a factor of at least three, four or five. In another embodiment the concentrated medium from at least two medium containers (53) is mixed with water or buffer from the water/buffer supply (55) prior to being fed to the cell culture vessel (50).

The inline buffer dilution system may also employ two or more concentrated wash, elution, cleaning and/or equilibration buffer containers, e.g. containing different buffer components. In this case, the system may be constructed such that different buffer components having different concentrations are led into a single mixing chamber by different inlets at different flow rates and diluted in the mixing chamber with water or buffer to the desired concentration, where after the diluted mixture is provided to the first and second chromatography units. Another option, in the case of multiple buffer containers, is for each buffer container to be connected to a separate mixing chamber for dilution with water or buffer. The separate mixing chambers can be further connected to a common mixing chamber, wherein diluted buffer from two or more individual separate mixing chambers is mixed together before being led into the first and second chromatography units via a single inlet, or alternatively, diluted buffer from individual separate mixing chambers may be conveyed to the first and second chromatography units by way of multiple inlets, e.g. one inlet for each mixing chamber.

The use of two or more buffer containers may be advantageous in order to be able to further reduce container size, space requirements, etc., for example by using one container to hold one buffer component and another container to hold another buffer component. Another possibility is to have a first wash buffer comprising certain components in a concentrated form in one wash buffer container and a second wash buffer comprising other components in a concentrated form in a second wash buffer container.

Similarly, it may be advantageous to have two or more cleaning and/or equilibration buffer containers holding different cleaning compounds in different concentration for efficient cleaning and/or equilibration of the first and second chromatography units.

Since the elution buffer, in some cases, has to be prepared within very exact specification ranges for pH, conductivity and/or osmolality, the elution buffer may either be present in the container in a more concentrated form than the concentration that is provided to the first and second chromatography units or it may be present in the container in the same concentration as the concentration that is provided to the first and second chromatography units for eluting the biopolymer (i.e. as a working solution ready). In situations where the elution buffer is present in the container as a working solution ready buffer the outlet (22) of the elution buffer container (5) may be in direct fluid connection with the inlet (12) of the first chromatography unit (2) and/or with the inlet (14) of the second chromatography unit (3). In other words the outlet (22) of the elution buffer container (5) is directly connected with the inlet (12) of the first chromatography unit (2) and/or with the inlet (14) of the second chromatography unit (3). Another option is that the outlet (22) of the elution buffer container (5)) through an independent inlet of the of the inline buffer dilution system and the inline buffer dilution system is also in fluid connection with the inlet (12) of the first chromatography unit (2) and/or with the inlet (14) of the second chromatography unit (3) through an independent outlet of the of the inline buffer dilution system.

In one embodiment of the present invention the outlet (22) of the elution buffer container (5) is in direct fluid connection with the inlet (12) of the first chromatography unit (2) and/or with the inlet (14) of the second chromatography unit (3).

In another embodiment of the invention, the eluting system may comprise two or more washing, eluting, cleaning and equilibration buffer containers, each of which is in fluid connection with an inlet (26a) of the inline buffer dilution system.

The elution buffer may also be prepared from the concentrates by the inline buffer dilution system gradient elution or for stepwise elution. In gradient elution the elution buffer is changed continuously toward conditions favouring dissociation from the affinity ligand. In stepwise elution the elution buffer is changed stepwise, at one or several occasions Such a gradient may either simply be prepared from two stock solutions having for example different salt concentrations or pH's or it can be prepared form multi-component concentrates having for example both different metal ion concentrations, salt concentrations and pH's.

In one embodiment of the invention, the inline medium dilution system (56) may be connected to a sensor located within or outside the cell culture vessel that can measure the concentration or the amount of medium or of selected components or nutrients in the cell culture vessel. The inline dilution system may in this case be operated as an automated system, allowing the concentration or the amount of medium or selected medium components or nutrients in the cell culture vessel to e.g. be kept constant in the event the perfusion rate is changed or a bleed is made to decrease the cell density in the cell culture vessel, or to otherwise be regulated as desired.

The inline medium dilution system (56) and the inline buffer dilution system (9) may have inline monitoring and control of the dilution process using instrumentation such as mass flow meters and/or analytical instruments such as pH, conductivity or near-infrared (NIR) instrumentation. A programmable logic controller may integrate the operation and control of all components in the systems.

Cell Culture Medium

As used herein the term "medium" refers to a cell culture medium. Numerous cell culture media are known and commercially available. Such media typically have a composition which is adapted for cultivation of certain types of cells and may comprise salts, amino acids, vitamins, lipids, detergents, buffers, growth factors, hormones, cytokines, trace elements and carbohydrates. Examples of salts include magnesium salts, for example $MgCl_2 \times 6H_2O$, and iron salts, for example $FeSO_4 \times 7H_2O$, potassium salts, for example $KH_2PO_4$, KCl, sodium salts, for example $NaH_2PO_4$ or $Na_2HPO_4$, and calcium salts, for example $CaCl_2 \times 2H_2O$. Examples of amino acids are the 20 naturally occurring amino acids, for example histidine, glutamine, threonine, serine, methionine. Examples of vitamins include ascorbate, biotin, choline, myo-inositol, D-panthothenate and riboflavin. Examples of lipids include fatty acids, for example linoleic acid and oleic acid. Examples of detergents include Tween® 80 and Pluronic® F68. An example of a buffer is HEPES. Examples of growth factors/hormones/cytokines include IGF, hydrocortisone and (recombinant) insulin. Examples of trace elements include Zn, Mg and Se. Examples of carbohydrates include glucose, fructose, galactose and pyruvate. Examples of other components that may be included in the medium are soy peptone and ethanol amine. The skilled person will be familiar with suitable media and media supplements as well as suitable conditions with respect to specific expression cells and polypeptides of interest. Silicon-based antifoams and defoamers or nonionic surfactants such as coblock polymers of ethylene oxide/propylene oxide monomers may be added to the medium during fermentation.

The pH, temperature, dissolved oxygen concentration and osmolarity of the cell culture medium will depend on the particular type of cell, and will be chosen such that they are optimal for the growth and productivity of the cells in question. The person skilled in the art will know how to determine the optimal conditions such as pH, temperature, dissolved oxygen concentration and osmolarity for a given culture. Usually, the optimal pH for mammalian cells is between 6.6 and 7.6, the optimal temperature is between 30 and 39° C., and the optimal osmolarity is between 260 and 400 mOsm/kg. For microbial systems the pH may be between 3 and 8 and the temperature from 20 to 45° C.

The solubility of the different medium components varies considerably, as many of the components will have a high solubility and thus be easily dissolved in water whereas other components such as certain vitamins, amino acids, lipids and growth factors have a low solubility in water. For this reason, cell culture media are normally prepared by mixing together all the components as a ready-to-use composition.

In one embodiment of the present invention the medium is made such that components that are easily dissolved in water are prepared together in one lot, and components with a low solubility and that are difficult to dissolve in water are prepared together in another lot. The two (or more) lots are then separately dissolved in water so as to produce two (or more) concentrated media fractions having desired concentrations of the individual components. The concentrated media fractions may for example be prepared as solutions wherein the media components are 2 times, 3 times, 4 times, or 5 times or more, e.g. up to 10 times, as concentrated as the components in the culture vessel.

Cells

As used herein the term "cell" can include both prokaryotic and eukaryotic cells.

Expression of biopolymers, in particular polypeptides, for therapeutic use has been accomplished using bacteria, yeast and mammalian cells, and the skilled person will be familiar with numerous suitable expression cells for production of a given product. The cells expressing the biopolymer (e.g.

polypeptide) may thus be selected e.g. from the group consisting of *E. coli, Bacillus*, yeast of the genus of *Saccharomyces, Pichia, Aspergillus, Fusarium,* or *Kluyveromyces*, CHO (Chinese hamster ovary) cells, hybridomas, BHK (baby hamster kidney) cells, myeloma cells, HEK-293 cells, PER.C6® cells, amniosytes including human amniosytes such as CAP® and CAP-T® cell lines, human lymphoblastoid cells and mouse cells, such as NSO cells.

In the context of the present invention, the cells are preferably eukaryotic cells, in particular mammalian cells. In a preferred embodiment the cells are mammalian cells, e.g. selected from the group consisting of CHO (Chinese hamster ovary) cells, hybridomas, BHK (baby hamster kidney) cells, myeloma cells, HEK-293 cells, PER.C6® cells, human lymphoblastoid cells, NSO cells and amniosytes such as human amniosytes. In one embodiment, the cell is a CHO cell such as a CHO DG44 cell, for example under control of Chinese hamster EF-1α regulatory sequences.

Since the invention as described preferably operates using a high cell density, one may advantageously use a cell culture medium with a high cell density from one fermentation to re-start (i.e. seed) a new fermentation. A high viable cell density in this context is typically a density of at least 10 million cells/ml, preferably at least 20 million cells/ml, more preferably at least 30 million cells/ml, e.g. at least 40 million cells/ml, such as at least 50 million cells/ml.

In some cases it may be convenient to grow cells to a desired cell density in one bioreactor and then transfer the cells to a second bioreactor for inducing the expression of the polypeptide by adding an inducer (for cells that are under control of an inducible promoter) or by changing the temperature and/or the pH of the medium. In such case impurities may also be removed via the separation device of the first bioreactor using a desired flow rate and via the separation device of the second bioreactor using the same or a different desired flow rate.

Fermentation Process

As explained elsewhere herein, the system of the invention is preferably a continuous system, i.e. the fermentation is performed as continuous fermentation. In a preferred embodiment, the product produced by the method is a polypeptide, such as a protein, and the fermentation is performed as a perfusion process, i.e. a process in which a suspension cell culture in a bioreactor is continuously supplied with fresh medium while spent culture medium is continuously harvested, with cells being continuously filtered from the harvest stream and returned to the bioreactor to maintain a uniform cell density.

Except as otherwise described herein, the perfusion process may be performed as generally known in the art. A typical process may thus involve, following inoculation of the bioreactor, e.g. about 2-3 days or more in which the cells are grown without perfusion in order to obtain an initial desired cell density, followed by initiation of perfusion (i.e. harvest) at a low level of e.g. about 0.5-1 reactor volume per day, after which the perfusion rate is increased to e.g. about 1.5-3 reactor volumes per day once the cell density has increased further. The term "reactor volume" in this context will be understood as corresponding to the working cell culture vessel volume of the particular system. The process is continuously monitored as known in the art and as otherwise explained herein, such that growth conditions, medium concentration, cell density, pH etc. are maintained within desired specifications. Harvest of the biopolymer together with waste products starts when a desired cell density is achieved or when a desired level of biopolymer is present in the medium. As used herein the term "pre-determined level of cells and/or biopolymer" refers to such an achieved desired cell density or to a desired level of biopolymer or to both the achieved desired cell density and the desired level of biopolymer is present in the cell culture medium.

In one embodiment of the present invention the cell density in the cell culture vessel during the fermentation reaches at least 10 million cells per ml medium, e.g. at least 20 million cells per ml medium, such as at least 30 million cells per ml medium, such as at least 40 million cells per ml medium.

The level of the harvest stream for a given perfusion process, i.e. the level used for the majority of the fermentation, will be able to be determined by the skilled person taking into consideration the characteristics of the individual bioreactor system and process, but will often be in the range of from about 0.5 to about 3 reactor volumes per day, such as from about 1 to about 3 reactor volumes per day, e.g. from about 1.5 to about 2.5 reactor volumes per day. The perfusion process is often performed for about 3-6 weeks, but may last even longer, such as up to about 2 months or more.

Persons skilled in the art will be aware that the temperature of the medium in the cell culture vessel is a key factor for productivity of the cells, with a temperature in the range of about 30-38° C. often being optimal, and that it may be advantageous to employ a temperature reduction during the fermentation. Such procedures are well-known, in particular for mammalian cells such as CHO cells, and typically involve an initial fermentation phase at a first temperature of e.g. about 37° C. in order to obtain a desired cell density, followed by a reduction in temperature to, for example, about 32-35° C. for the remainder of the fermentation in order to increase expression of the polypeptide product and reduce cell division.

In one embodiment of the present invention the method for producing a biopolymer in a bioreactor arrangement of the present invention comprises:

(a) fermenting cells expressing the biopolymer in a suitable medium under suitable conditions until a pre-determined level of cells and/or biopolymer is reached in the cell culture vessel (50), (b) harvesting the biopolymer by removing medium comprising biopolymer and waste products via the product harvest module (51).

In another embodiment of the present invention the method for producing a biopolymer in a bioreactor arrangement of the present invention further comprising, a medium container (53), a water and/or buffer supply (55), an inline medium dilution system (56) for diluting concentrated medium from the medium container, the inline medium dilution system having an inlet (57) and an outlet (58), wherein the inlet is in fluid connection with the medium container (53) and the water/buffer supply (55), and wherein the outlet (58) is in fluid connection with the culture vessel (50), wherein during fermentation, the method further comprises: adding concentrated medium from the medium container (53) and water or buffer from the water/buffer supply (55) to an inlet (57) of the inline medium dilution system (56) to result in diluted medium, and feeding the diluted medium containing nutrients to the cell culture vessel (50) through an outlet (58) to replenish nutrients consumed by the cells and to compensate for medium removed for harvesting of the biopolymer.

Capturing, Washing and Eluting Process

During operation of the present chromatography system, medium comprising biopolymer and waste products are provided from the product harvest module (51) to the first and/or second chromatography units (2) and/or (3) and the biopolymer is captured by the affinity ligand e.g. resin or filter whereby binding sites for the absorbing biopolymer get occupied and the binding capacity decreases. The method of capturing the biopolymer onto the first and second chromatography units is based on operating two chromatography units independent or in series such that biopolymer escaping the first chromatography unit will be caught on the second chromatography unit. When the first chromatography unit is loaded until a pre-determined level of binding capacity, it is detached from the second chromatography unit, washed and the biopolymer is eluted. Optionally, it is subsequently cleaned and equilibrated before it is attached in front of the second chromatography. When the second chromatography is loaded until a pre-determined level of binding capacity with biopolymer it is detached from the first chromatography unit, washed and the biopolymer is eluted.

As used herein the term "pre-determined level of binding capacity" generally refers to a desired level of binding capacity of the first and/or second chromatography unit. The binding capacity of an affinity ligand may be determined empirically and is for example dependent on the loading conditions e.g. flow rate and the temperature. As used herein the term "binding capacity" refers to the amount of biopolymer that the ligand (e.g., beads packed in a column) can bind under equilibrium conditions if every available binding site on the beads is utilized. The pre-fix "first", "second", "third", fourth" and "fifth" is intended to mean that the pre-determined levels are selected individually, and may be different or may be the same.

The pre-determined levels of binding capacity may independently be set such that the resin for example is loaded to about 30%400%, including greater than about 30%, greater than about 40%, greater than about 50%, greater than about 60%, greater than about 70%, greater than about 80%, greater than about 90%, and greater than about 98%, of its binding capacity. The pre-determined levels of binding capacity may also be set independently such that only 0.5% at the most, 1% at the most, 2% at the most, 5% at the most, 10% at the most, 15% at the most or 20% at the most of the biopolymer in the medium passes through the outlet (13) or (15) of the first and second chromatography units (2) or (3) to a waste or holding container. Typically, the first, second, third, fourth and fifth pre-determined level of binding capacity will be determined independently, and adjusted such that the pre-determined level of binding capacity is reached after a specific time period of loading. Such a time period may be set from about 15 minutes to about 24 hours, such as from about 30 minutes to about 24 hours, such as from about 1 hour to about 24 hours, such as from about 2 hours to about 24 hours, such as from about 4 hours to about 24 hours, such as from about 6 hours to about 24 hours, such as from about 8 hours to about 24 hours, such as from about 10 hours to about 24 hours, such as from about 12 hours to about 24 hours, such as from about 1 hour to about 20 hours, such as from about 2 hours to about 18 hours, such as from about 2 hours to about 16 hours, such as from about 2 hours to about 12 hours, such as from about 2 hours to about 10 hours, such as from about 2 hours to about 8 hours, such as from about 2 hours to about 6 hours.

However, the first pre-determined level of binding capacity will typically be set such that it allows sufficient time for washing, eluting and optionally cleaning and equilibrating the first chromatography unit (2) such that the first chromatography unit (2) can be connected to the second chromatography unit (3), before the first chromatography unit (2) becomes saturated or overloaded with biopolymer and the biopolymer escapes from being captured onto the first chromatography unit (2). In one embodiment of the present invention the first pre-determined level of binding capacity is set to avoid biopolymer in the medium through the outlet (13) of the first chromatography unit (2) and/or the outlet (15) of the second chromatography unit (3). In a further embodiment the first pre-determined level of binding capacity is set so that the resin is loaded to about 30%400% of its binding capacity. In a still further embodiment the first pre-determined level of binding capacity is set so that 20% at the most of the biopolymer in the medium passes through the outlet (13) of the first chromatography unit (2) to a waste or holding container.

The second pre-determined level of binding capacity of step (d) may typically be set such that the first chromatography unit (2) becomes fully saturated with biopolymer, while allowing sufficient binding capacity of the second chromatography unit (3) such that the first chromatography unit (2) can be washed, eluted, cleaned and equilibrated before biopolymer begin to escape from being captured on the second chromatography unit (3). In one embodiment of the present invention the second pre-determined level of binding capacity is set to avoid biopolymer in the medium through the outlet (13) of the first chromatography unit (2) and/or through the outlet (15) of the second chromatography unit (3). In a further embodiment the second pre-determined level of binding capacity is set so that the resin is loaded to about 30%-100% of its binding capacity. In a still further embodiment the second pre-determined level of binding capacity is set so that 20% at the most of the biopolymer in the medium passes through the outlet (15) of the second chromatography unit (3) to a waste or holding container.

The third pre-determined level of binding capacity of step (e) may typically be set such that it allows sufficient time for washing, eluting and optionally cleaning and equilibrating the first chromatography unit (2) such that first chromatography unit (2) can be connected to the second chromatography unit (3), before the second chromatography unit (3) becomes saturated or overloaded with biopolymer and the biopolymer escapes from being captured onto the second chromatography unit (3). In one embodiment of the present invention the third pre-determined level of binding capacity is set to avoid biopolymer in the medium through the outlet (13) of the first chromatography unit (2) and/or through the outlet (15) of the second chromatography unit (3). In a further embodiment the third pre-determined level of binding capacity is set so that the resin is loaded to about 30%400% of its binding capacity. In a still further embodiment the third pre-determined level of binding capacity is set so that 20% at the most of the biopolymer in the medium passes through the outlet (15) of the second chromatography unit (3) to a waste or holding container.

The fourth pre-determined level of binding capacity of step (f) may typically be set such that the second chromatography unit (3) becomes fully saturated with biopolymer, while allowing sufficient binding capacity of the first chromatography unit (2) such that the second chromatography unit (3) can be washed, eluted, cleaned and equilibrated before biopolymer begin to escape from being captured on the first chromatography unit (2). In one embodiment of the present invention the fourth pre-determined level of binding capacity is set to avoid biopolymer in the medium through the outlet (13) of the first chromatography unit (2) and/or through the outlet (15) of the second chromatography unit (3). In a further embodiment the fourth pre-determined level of binding capacity is set so that the resin is loaded to about 30%400% of its binding capacity. In a still further embodiment the fourth pre-determined level of binding capacity is set so that 20% at the most of the biopolymer in the medium passes through the outlet (13) of the first chromatography unit (2) to a waste or holding container.

The fifth pre-determined level of binding capacity of step (g) may typically be set such that it allows sufficient time for washing, eluting and optionally cleaning and equilibrating the second chromatography unit (3) such that second chromatography unit (3) can be connected to the first chromatography unit (2), before the first chromatography unit (2) becomes saturated or overloaded with biopolymer and the biopolymer escapes from being captured onto the second chromatography unit (3). In one embodiment of the present invention the fifth pre-determined level of binding capacity is set to avoid biopolymer in the medium through the outlet (13) of the first chromatography unit (2) and/or through the outlet (15) of the second chromatography unit (3). In a further embodiment the fifth pre-determined level of binding capacity is set so that the resin is loaded to about 30%-100% of its binding capacity. In a still further embodiment the fifth pre-determined level of binding capacity is set so that 20% at the most of the biopolymer in the medium passes through the outlet (13) of the first chromatography unit (2) to a waste or holding container.

As used herein the term "specified setting" is intended to encompass any specified time period necessary for the biopolymer that is un-captured by the first chromatography unit to be captured on the second chromatography unit. It is also intended to encompass any specified amount of medium or biopolymer that passes un-captured by the first chromatography unit to be captured on the second chromatography unit. In an embodiment the specified setting is selected from a specified time, a specified volume, a specified amount of biopolymer, and a specified concentration of biopolymer. In one embodiment the specified setting is a specified time. In an other embodiment the specified setting is a specified volume. In a further embodiment the specified setting is a specified amount of biopolymer such as a specified concentration of biopolymer.

An advantage of operating the first and second chromatography units in series according to the present invention is that the first chromatography unit (2) can be loaded until most or all binding sites for absorbing the biopolymer are occupied. When more and more of the binding sites get occupied by the biopolymer there are less and less binding sites available for waste products i.e. impurities. Moreover, since the biopolymer has higher affinity for the affinity ligand e.g. the resin waste products get displaced from the chromatography unit such that a much more pure biopolymer can be produced.

The washing steps may be carried out using a single wash buffer or by using several wash buffers of different composition. The pre-determined levels of washing may be determined by monitoring the amount of waste components that flow through the chromatography unit using suitable detectors such UV detectors of optical density detectors. Often, the pre-determined levels of washing is determined in initial experiments and converted to the amount of wash buffer necessary for the desired pre-determined level of washing to be obtained. Typically, wash buffers are used in volumes of 3 to 20 times the volume of the chromatography unit. The skilled person knows how to select suitable wash buffers depending on the chromatography unit used and the biopolymer to be produced. Typical example of wash buffers are 15-50 mM Na-phosphate with 0.15-0.5 M NaCl at pH 6.5-7.5.

In one embodiment of the present invention the first pre-determined level of washing is set such that at least 50%, such that at least 60%, such that at least 70%, such that at least 80%, such that at least 85%, such that at least 90%, such that at least 90% of the impurities present on the first chromatography unit (2) has passed through the outlet (13) of the first chromatography unit (2).

In another embodiment the second pre-determined level of washing is set such that at least 50%, such that at least 60%, such that at least 70%, such that at least 80%, such that at least 85%, such that at least 90%, such that at least 90% of the impurities present on the second chromatography unit (3) has passed through the outlet (15) of the second chromatography unit (3).

In one embodiment of the present invention the third pre-determined level of washing is set such that at least 50%, such that at least 60%, such that at least 70%, such that at least 80%, such that at least 85%, such that at least 90%, such that at least 90% of the impurities present on the first chromatography unit (2) has passed through the outlet (13) of the first chromatography unit (2).

In another embodiment the fourth pre-determined level of washing is set such that at least 50%, such that at least 60%, such that at least 70%, such that at least 80%, such that at least 85%, such that at least 90%, such that at least 90% of the impurities present on the second chromatography unit (3) has passed through the outlet (15) of the second chromatography unit (3).

The elution steps may be carried out using a single elution buffer, by using several elution buffers of different composition or by using an elution gradient. The pre-determined levels of elution may be determined by monitoring the amount of biopolymer that flow through the chromatography unit using suitable detectors and set to when no biopolymer or nearly no biopolymer is detected. Often, the pre-determined levels of elution is determined in initial experiments and converted to the amount of elution buffer necessary for the desired pre-determined level of washing to be obtained. Typically, elution buffers are used in volumes of 3 to 20 times the volume of the chromatography unit. The skilled person knows how to select suitable elution buffers depending on the chromatography unit used and the biopolymer to be produced. Examples of elution buffers include solution with low pH, solution with low or high salt concentrations, glycine-HCl buffers, buffers containing ethylene glycol and citrate buffers having a pH from about 3 to about 9.

In one embodiment of the present invention the first pre-determined level of eluating is set such that at least 50%, such that at least 60%, such that at least 70%, such that at least 80%, such that at least 85%, such that at least 90%, such that at least 95% of the biopolymer present on the first chromatography unit (2) has passed through the outlet (13) of the first chromatography unit (2).

In an other embodiment the second pre-determined level of eluating is set such that at least 50%, such that at least 60%, such that at least 70%, such that at least 80%, such that at least 85%, such that at least 90%, such that at least 95% of the biopolymer present on the second chromatography unit (3) has passed through the outlet (15) of the second chromatography unit (3).

In further embodiment the third pre-determined level of eluating is set such that at least 50%, such that at least 60%, such that at least 70%, such that at least 80%, such that at least 85%, such that at least 90%, such that at least 95% of the biopolymer present on the first chromatography unit (2) has passed through the outlet (13) of the first chromatography unit (2).

In further embodiment the fourth pre-determined level of eluating is set such that at least 50%, such that at least 60%, such that at least 70%, such that at least 80%, such that at least 85%, such that at least 90%, such that at least 95% of the biopolymer present on the second chromatography unit (3) has passed through the outlet (15) of the second chromatography unit (3).

The method for producing a biopolymer according to the present invention is based on repeatedly loading, washing and eluting the biopolymer. Consequently, the first and second chromatography units (2) and (3) has to be repeatedly connected and disconnected. However, during the first round of the capturing the biopolymer, the first chromatography unit (2) may either be operated alone, i.e. where the fluid connection from the outlet (13) of the first chromatography unit (2) to the inlet (14) of the second chromatography unit (3) is closed by the third valve means (33) or it may be operated as connected with the first chromatography unit (2), i.e. wherein the fluid connection from the outlet (13) of the first chromatography unit (2) to the inlet (14) of the second chromatography unit (3) is open by the third valve means (33).

In one embodiment of the present invention step (c) can be conducted leading a medium comprising the biopolymer and waste products through the fluid connection from the outlet (16) of the product harvest module (51) to the inlet (12) of the first chromatography unit (2) wherein the biopolymer is captured on the first chromatography unit (2), and medium and waste products continues through the outlet (13) of the first chromatography unit (2) until a first pre-determined level of saturated binding capacity is reached in the first chromatography unit (2), wherein the fluid connection from the outlet (16) of the product harvest module (51) to the inlet (14) of the second chromatography unit (3) is closed by the second valve means (32) and wherein the fluid connection from the outlet (13) of the first chromatography unit (2) to the inlet (14) of the second chromatography unit (3) is open by the third valve means (33).

In another embodiment of the present invention the chromatography system may be arranged using disposable chromatography units, also called single use or chromatography units that are discarded after the biopolymer has been eluted from the chromatography units and replaced new chromatography units after their use. In a further embodiment of the present invention the chromatography system is arranged using multi use chromatography units that are repeatedly loaded, eluted, cleaned and regenerated.

Cleaning of the first and second chromatography units may be carried out using a single cleaning buffer or by using several cleaning buffers of different composition.

The pre-determined levels of cleaning may be determined by monitoring the amount of waste products that flow through the chromatography unit using suitable detectors. Often, the pre-determined levels of elution is determined in initial experiments and converted to the amount of cleaning buffer necessary for the desired pre-determined level of cleaning to be obtained. Typically, cleaning buffers are used in volumes of 3 to 20 times the volume of the chromatography unit. The skilled person knows how to select suitable cleaning buffers depending on the chromatography unit used and the biopolymer to be produced. Typical examples of cleaning buffers include 0.1-0.5 M NaOH.

During operation of multi use chromatography units for purification of antibodies, such as protein A based columns, waste products tends to accumulate in the upper part of the chromatography units. In such a situation it may be an advantages to provide the cleaning buffer to the outlets (13) and (15) of the first chromatography unit (2) and (3) leading it through the first chromatography unit (2) and (3) and through the inlets (12) and (14) of the first and second chromatography units, to for example a waste container or holding tank, to facility efficient cleaning of the first and second chromatography units.

In one embodiment of the present invention after step (ii);
(iia) cleaning the first chromatography unit (2) with a specified concentration of water and buffer by leading cleaning buffer through the fluid connection from the outlet (23) of the cleaning buffer container (6) to the inlet (12) of the first chromatography unit (2), through the first chromatography unit (2), and through the outlet (13) of the first chromatography unit (2), until a first pre-determined level of cleaning is reached, and wherein after step (iv);
(iva) cleaning the second chromatography unit (3) with a specified concentration of water and buffer by leading cleaning buffer through the fluid connection from the outlet (23) of the cleaning buffer container (6) to the inlet to the inlet (14) of the second chromatography unit (3), through the second chromatography unit (3), and through the outlet (15) of the second chromatography unit (3), until a second pre-determined level of cleaning is reached.

In another embodiment after step (ii);
(iib) cleaning the first chromatography unit (2) with a specified concentration of water and buffer by leading cleaning buffer through the fluid connection from the outlet (23) of the cleaning buffer container (6) to the outlet (13) of the first chromatography unit (2), through the first chromatography unit (2), and through the inlet (12) of the first chromatography unit (2), until a third pre-determined level of cleaning is reached and, wherein after step (iv);
(ivb) cleaning the second chromatography unit (3) with a specified concentration of water and buffer by leading cleaning buffer through the fluid connection from the outlet (23) of the cleaning buffer container (6) to the outlet (15) of the second chromatography unit (3), through the second chromatography unit (3), and through the inlet (14) of the second chromatography unit (3), until a fourth pre-determined level of cleaning is reached.

In a further embodiment after step (ii);
(iia) cleaning the first chromatography unit (2) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the inlet (12) of the first chromatography unit (2), through the first chromatography unit (2), and through the outlet (13) of the first chromatography unit (2), until a fifth pre-determined level of cleaning is reached, wherein the fluid connection from the outlet (27) of the inline buffer dilution system (9) to the inlet (14) of the second chromatography unit (3) is closed by the eleventh valve means (41) and, wherein after step (iv);
(iva) cleaning the second chromatography unit (3) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the inlet (14) of the second chromatography unit (3), through the second chromatography unit (3), and through the outlet (15) of the second chromatography unit (3), until a sixth pre-determined level of cleaning is reached, wherein the fluid connection from the outlet (27) of the inline buffer dilution system (9) to the inlet (12) of the first chromatography unit (2) is closed by the tenth valve means (40).

In a still further embodiment after step (ii);
(iib) cleaning the first chromatography unit (2) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the outlet (13) of the first chromatography unit (2), through the first chromatography unit (2), and through the inlet (12) of the first chromatography unit (2), until a seventh pre-determined level of cleaning is reached, wherein the fluid connection from the outlet (27) of the inline buffer dilution system (9) to the inlet (12) of the first chromatography unit (2) is closed by the tenth valve means (40) and, wherein after step (iv);
(ivb) cleaning the second chromatography unit (3) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the outlet (15) of the second chromatography unit (3), through the second chromatography unit (3), and through the inlet (14) of the second chromatography unit (3), until a eight pre-determined level of cleaning is reached, wherein the fluid connection from the outlet (27) of the inline buffer dilution system (9) to the inlet (14) of the second chromatography unit (3) is closed by the eleventh valve means (41).

The steps of cleaning (iia), (iva), (iib) and (ivb) the first and second chromatography units (2) and (3) may be followed by steps of equilibrating the chromatography for making them ready for receiving the biopolymer. Typical examples of equilibration buffers include 5-40 mM sodium phosphate with 20-250 mM NaCl at pH 6.5-7.5.

In one embodiment of the present invention after step (iia) or (iib);
(iic) equilibrating the first chromatography unit (2) with a specified concentration of water and buffer by leading equilibration buffer through the fluid connection from the outlet (24) of the equilibration buffer container (7) to the inlet (12) of the first chromatography unit (2), through the first chromatography unit (2), and through the inlet (12) of the first chromatography unit (2), until a first pre-determined level of equilibration is reached, and wherein after step (iva) or (ivb);
(ivc) equilibrating the second chromatography unit (3) with a specified concentration of water and buffer by leading equilibration buffer through the fluid connection from the outlet (24) of the equilibration buffer container (7) to the inlet (12) of the first chromatography unit (2), through the first chromatography unit (2), and through the outlet (13) of the first chromatography unit (2), until a second pre-determined level of equilibration is reached.

In a further embodiment the chromatography system further comprises,
a water supply (8) having an outlet (25), and an inline buffer dilution system (9) having an inlet (26a) and an outlet (27), wherein the outlet (21) of the wash buffer container (4) is in fluid connection with the inlet (26a) of the inline buffer dilution system (9) and wherein a fifth valve means (35) is located between the outlet (21) of the wash buffer container (4) and the inlet (26a) of the inline buffer dilution system (9), wherein the outlet (22) of the elution buffer container (5) is in fluid connection with the inlet (26a) of the inline buffer dilution system (9) and wherein a sixth valve means (36) is located between the outlet (22) of the elution buffer container (5) and the inlet (26a) of the inline buffer dilution system (9),
optionally, wherein the outlet (23) of the cleaning buffer container (6) is in fluid connection with the inlet (26a) of the inline buffer dilution system (9) and wherein a seventh valve means (37) is located between the outlet (23) of the cleaning buffer container (6) and the inlet (26a) of the inline buffer dilution system (9),
optionally, wherein the outlet (24) of the equilibration buffer container (7) is in fluid connection with the inlet (26a) of the inline buffer dilution system (9) and wherein an eighth valve means (38) is located between the outlet (24) of the equilibration buffer container (7) and the inlet (26a) of the inline buffer dilution system (9),
wherein the outlet (25) of the water supply (8) is in fluid connection with the inlet (26a) of the inline buffer dilution system (9) or is in fluid connection with a separate inlet (26b) of the inline buffer dilution system (9) and wherein a ninth valve means (39) is located between the outlet (25) of the water supply (8) and the inlet (26a) or the separate inlet (26b) of the inline buffer dilution system (9); and wherein the outlet (27) of the inline buffer dilution system (9) is in fluid connection with the inlet (12) of the first chromatography unit (2) and in fluid connection with the inlet (14) of the second chromatography unit (3), wherein a tenth valve means (40) is located between the outlet (27) of the inline buffer dilution system (9) and the inlet (12) of the first chromatography unit (2), and an eleventh valve means (41) is located between the outlet (27) of the inline buffer dilution system (9) and inlet (14) of the second chromatography unit (3).

wherein during or after step e)

(i) washing the first chromatography unit (2) with a specified concentration of water and buffer by leading concentrated wash buffer through the fluid connection from the outlet (21) of the wash buffer container (4) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (22) of the elution buffer container (5) to the inlet (26a) of the inline buffer dilution system (9) is closed by the sixth valve means (36), and leading the diluted wash buffer through the outlet (27) of the inline buffer dilution system (9) to the inlet (12) of the first chromatography unit (2), through the first chromatography unit (2), and through the outlet (13) of the first chromatography unit (2), until a third pre-determined level of washing is reached, wherein the fluid connection from the outlet (27) of the inline buffer dilution system (9) to the inlet (14) of the second chromatography unit (3) is closed by the eleventh valve means (41), (ii) when the third pre-determined level of washing is reached, eluting the biopolymer from the first chromatography unit (2) by leading:

(a1) concentrated elution buffer through the fluid connection from the outlet (22) of the elution buffer container (5) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) or alternatively by leading:

(a2) a working solution ready elution buffer through the fluid connection from the outlet (22) of the elution buffer container (5) to the inlet (26a) of the inline buffer dilution system (9), wherein the fluid connection from the outlet (21) of the wash buffer container (4) to the inlet (26a) of the inline buffer dilution system (9) is closed by the fifth valve means (35) and, wherein when the working solution ready elution buffer is used the fluid connection from the outlet (25) of the water supply (8) to the inlet (26a) or the inlet (26b) of the inline buffer dilution system (9) is closed by the ninth valve means (39) and leading the working solution ready elution buffer from the outlet (27) of the inline buffer dilution system (9) to the inlet (12) of the first chromatography unit (2), through the first chromatography unit (2), and through the outlet (13) of the first chromatography unit (2), until a third pre-determined level of eluating is reached, and collecting the eluate, wherein the fluid connection from the outlet (27) of the inline buffer dilution system (9) to the inlet (14) of the second chromatography unit (3) is closed by the eleventh valve means (41), and wherein during or after step g)

(iii) washing the second chromatography unit (3) with a specified concentration of water and buffer by leading concentrated wash buffer through the fluid connection from the outlet (21) of the wash buffer container (4) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9), wherein the fluid connection from the outlet (22) of the elution buffer container (5) to the inlet (26a) of the inline buffer dilution system (9) is closed by the sixth valve means (36), and leading the diluted wash buffer through the outlet (27) of the inline buffer dilution system (9) to the inlet (14) of the second chromatography unit (3), through the second chromatography unit (3), and through the outlet (15) of the second chromatography unit (3), until a fourth pre-determined level of washing is reached, wherein the fluid connection from the outlet (27) of the inline buffer dilution system (9) to the inlet (12) of the first chromatography unit (2) is closed by the tenth valve means (40), (iv) when the fourth pre-determined level of washing is reached, eluting the biopolymer from the second chromatography unit (3) by leading:

(b1) concentrated elution buffer through the fluid connection from the outlet (22) of the elution buffer container (5) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) or alternatively by leading:

(b2) a working solution ready elution buffer through the fluid connection from the outlet (22) of the elution buffer container (5) to the inlet (26a) of the inline buffer dilution system (9), wherein the fluid connection from the outlet (21) of the wash buffer container (4) to the inlet (26a) of the inline buffer dilution system (9) is closed by the fifth valve means (35) and, wherein when the working solution ready elution buffer is used the fluid connection from the outlet (25) of the water supply (8) to the inlet (26a) or the inlet (26b) of the inline buffer dilution system (9) is closed by the ninth valve means (39) and leading the diluted elution buffer through the outlet (27) of the inline buffer dilution system (9) to the inlet (14) of the second chromatography unit (3), through the second chromatography unit (3), and through the outlet (15) of the second chromatography unit (3), until a fourth pre-determined level of eluating is reached, and collecting the eluate, wherein the fluid connection from the outlet (27) of the inline buffer dilution system (9) to the inlet (12) of the first chromatography unit (2) is closed by the tenth valve means (40).

In a still further embodiment after step (iia) or (iib);

(iic) equilibrating the first chromatography unit (2) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the inlet (12) of the first chromatography unit (2), until a third pre-determined level of equilibration is reached, wherein the fluid connection from the outlet (27) of the inline buffer dilution system (9) to the inlet (14) of the second chromatography unit (3) is closed by the eleventh valve means (41),
and wherein after step (iva) or (ivb);
(ivc) equilibrating the second chromatography unit (3) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the outlet (13) of the first chromatography unit (2), until a fourth pre-determined level of equilibration is reached, wherein the fluid connection from the outlet (27) of the inline buffer dilution system (9) to the inlet (14) of the second chromatography unit (3) is closed by the valve means (41).

The temperature of the medium and the wash, elution, cleaning and equilibration buffer may have an influence on the stability of the biopolymer and also on the binding of the biopolymer to the first and second chromatography units. The temperature may also have an influence on how impurities such as residual DNA and host cell proteins binds to the protein A ligand. The skilled person knows how to select suitable temperature condition for operating the chromatography system.

In one embodiment the medium in the product harvest module may be kept at a temperature of e.g. 28-38° C., such as about 32° C. or such as about 35° C. for enhancing the affinity to the first or second chromatography unit or both. In another embodiment the wash, elution, cleaning and/or equilibration buffers are used at a temperature of e.g. 28-38° C., such as about 32° C. or such as about 35° C. In a further embodiment the wash, elution, cleaning and/or equilibration buffers are used at a temperature in the range of 1-10° C. In another embodiment the wash, elution, cleaning and/or equilibration buffers are used at a temperature in the range of 10-30° C. In a further embodiment the medium in the product harvest module has a temperature of e.g. 28-38° C. and the wash, elution, cleaning and/or equilibration buffers are used at a temperature in the range of 1-10° C. in a still further embodiment the wash, elution, cleaning and/or equilibration buffers are used at a temperature in the range of from 1-40° C., such as from 20-40° C., such as from 30-40° C., such as from 1-10° C., such as from 5-20° C.

In a further embodiment the chromatography system and the inline medium dilution system (56) is kept at a temperature of e.g. 28-38° C., such as about 32° C. or such as about 35° C. In a preferred embodiment of the present invention the chromatography system is kept at a temperature of e.g. 28-38° C., such as about 32° C. or such as about 35° C. for enhancing removal of residual DNA and/or host cell protein.

The isolated product (e.g. polypeptide) of interest produced using the system and method of the invention may be further purified for removal of residual impurities such as host cell proteins, host cell DNA, protein A residues, viruses and/or aggregated antibodies, by methods known in the art for the given product, formulated into a final commercially relevant composition of interest (e.g. a pharmaceutical composition), and packaged in a suitable container.

DETAILED DRAWING DESCRIPTION

The following non-limiting drawing descriptions are for example purposes only and is not intended to limit the present invention in any way.

A bioreactor arrangement of the invention is illustrated schematically in FIG. 1, and includes, a cell culture vessel (50) with a product harvest module (51) for removing the biopolymer product along with cells, impurities and medium having an outlet (16) and with dashed lines, a medium container (53), an impurity filter unit (54) for separating out undesired purities, and a bleed outlet (52) that allows medium containing cells, cell debris and impurities to be removed from the cell culture vessel (50). Medium from the medium container (53) is in fluid connection with the cell culture vessel (50) and is introduced via inlet (59) of the medium container (53). Also attached to the cell culture vessel (50) is a bleed outlet (52) that may either be constructed as a separate unit or it may be built together as a single unit with the product harvest module (51). The outlet (16) of the product harvest module (51) is in fluid connection with a first chromatography unit (2) having an inlet (12) and an outlet (13) and a second chromatography unit (3) having an inlet (14) and an outlet (15). The outlet (13) of the first chromatography unit (2) and the outlet (15) of the second chromatography unit (3) are in fluid connection with a waste container (17) having and an inlet (29) and an eluate container (18) having an inlet (28) (shown with dashed lines). Each of the inlets (12) and (14), the outlet (16) or the fluid connection have at least one valve means (31, 32). In addition, the inlet (12) of the first chromatography unit (2) is in fluid connection with the outlet (15) of the second chromatography unit (3), and the inlet (14) of the second chromatography unit (3) is in fluid connection with the outlet (13) of first chromatography unit (2) through connection lines connecting outlet (13) with inlet (14) and outlet (15) with inlet (12), and each of the outlets (13) and (15) or the corresponding fluid connections have at least one valve means (33, 34). The outlet (13) of the first chromatography unit (2) is also in liquid connection with the inlet (29) of the waste container (17) (shown with dashed lines). Also shown is a wash buffer container (4) having an outlet (21), an elution buffer container (5) having an outlet (22) and with dashed lines (indicating that this is optional) a cleaning buffer container (6) having an outlet (23) and an equilibration buffer container (7) having an outlet (24), all of which are in fluid connection with the inlet (12) of the first chromatography unit (2) and the inlet 14 of the second chromatography unit (3) and the outlet (13) of the first chromatography unit (2) and the outlet (15) of the second chromatography unit (3). Each of the inlets (12) and (14), the outlets (13, 15, 21, 22, 23, 24) or the fluid connection have at least one valve means (40b, 41b).

Figure 2:
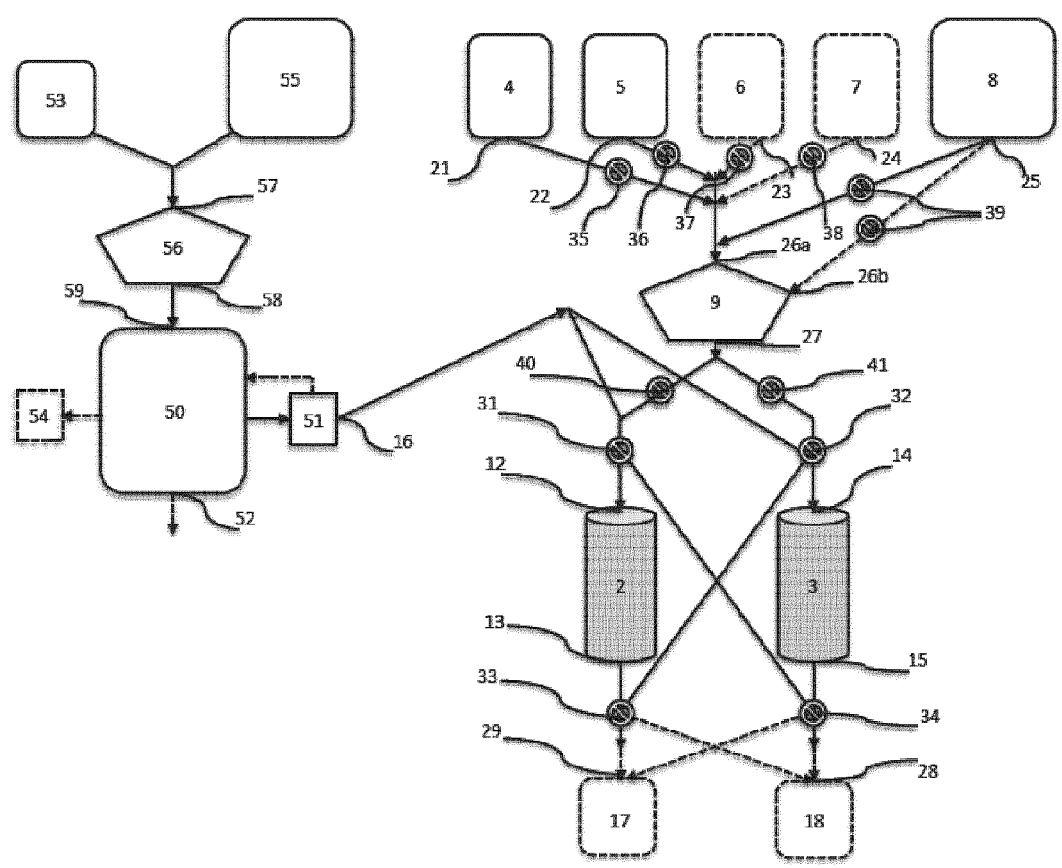
FIG. 2 is a schematic illustration of an alternative bioreactor arrangement according to the present invention employing an inline medium and buffer dilution system.

FIG. 2 shows an alternative embodiment of the bioreactor arrangement illustrated in FIG. 1. In FIG. 2 the bioreactor arrangement includes a medium container (53) and a water/buffer container (55), both of which are in fluid connection with an inlet (57) of a inline medium dilution system (56). The outlet (58) of the inline medium dilution system (56) is in fluid connection with the inlet (59) of the cell culture vessel (50). Water or buffer may in addition optionally be led directly from the water/buffer container (55) to the cell culture vessel (50) (illustrated by the dashed line between the two). In connection with the cell culture vessel (50) is a product harvest module (51) having an outlet (16). In a perfusion system, cells that are removed from the cell culture vessel (50) via the product harvest module (51) are optionally returned to the cell culture vessel (50) (dashed line from (51) to (50)). Connected to the cell culture vessel (50) is optionally also an impurity filter unit (54) for separating out undesired purities, and optionally a separate bleed outlet (52). As explained above, the bleed outlet (52) may either be constructed as a separate unit or it may be built together as a single unit with the product harvest module (51).

The outlet (16) of the product harvest module (51) is fluid connection with a first chromatography unit (2) having an inlet (12) and an outlet (13) and a second chromatography unit (3) having an inlet (14) and an outlet (15). Also shown is a wash buffer container (4) having an outlet (21), an elution buffer container (5) having an outlet (22), a water supply (8) having an outlet (25) and with dashed lines a cleaning buffer container (6) having an outlet (23) and an equilibration buffer container (7) having an outlet (24), all of which are in fluid connection with an inline buffer dilution system (9) having an inlet (26*a*) and an outlet (27), through connection lines connecting the outlets (21, 22, 23, 24, 25) to the inlet (26*a*) of the inline buffer dilution system. Each of the outlets (21, 22, 23, 24, 25) or the corresponding fluid connection(s) also have at least one valve means (35, 36, 37, 38, 39) for regulating the flow from each of the containers to the inline buffer dilution system. The dashed lines representing the cleaning buffer container (6), the equilibration buffer container (7) and the corresponding fluid connection indicates that these components are optional features of the system. Moreover, the fluid connection connecting the outlet (25) of the water supply (8) to the inlet (26*a*) of the inline buffer dilution system may either be using the same inlet as the connection lines connecting the outlets (21, 22, 23, 23, 24) with inlet (26*a*) or alternatively, as shown with a dashed line, be using a separate inlet (26*b*).

The outlet (27) of the inline dilution buffer system (9) is in fluid connection with the inlet (12) of first chromatography unit (2) and the inlet (14) of the second chromatography unit (3) through fluid connection connecting outlet (27) wherein valve means (40) and (41) are located between the outlet (27) of the inline dilution buffer system (9) and the inlet (12) of the first chromatography unit (2) and the inlet (14) of the second chromatography unit (3). The outlet (27) of the inline dilution buffer system (9) is also in fluid connection with the outlet (13) of the first chromatography unit (2) and the outlet (15) of the second chromatography unit (3). Each of the inlets (12) and (14), the outlet (16) or the fluid connections connecting the inlets (12) and (14) with the outlet (16), have at least one valve means (31, 32). In addition, the inlet (12) of the first chromatography unit (2) is in fluid connection with the outlet (15) of the second chromatography unit (3), and the inlet (14) of the second chromatography unit (3) is in fluid connection with the outlet (13) of the first chromatography unit (2) through connection lines connecting outlet (13) with inlet (14) and outlet (15) with inlet (12), and each of the outlets (13) and (15) or the corresponding fluid connections have at least one valve means (33, 34). The outlet (13) of the first chromatography unit (2) is also in liquid connection with the inlet (29) of the waste container (17) and the inlet (28) of the eluate container (18) through fluid connection connecting the outlet (13) with the inlet (29) and the inlet (28) with outlet (13) (showed with dashed lines).

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

Recitation of ranges of values herein are merely intended to serve as a short method of referring individually to each separate value falling within the range, unless other-wise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about", where appropriate).

All methods described herein can be performed in any suitable order unless other-wise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context. Thus, "a" and "an" and "the" may mean at least one, or one or more.

The term "and/or" as used herein in connection with a selection from a list is intended to include each of the individual. For instance the first chromatography unit and/or second chromatography unit (2) and/or (3) is intended to include either the first chromatography unit (2) or the second chromatography unit (3) or both the first and the second chromatography unit.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter re-cited in the aspects or claims presented herein to the maximum extent permitted by applicable law.

The features disclosed in the foregoing description may, both separately and in any combination thereof, be material for realizing the invention in diverse forms thereof.

EXAMPLES

Example 1 is directed to experiments regarding dynamic binding capacity of protein A chromatography and assessing the quality of the purification step in relation to residual host cell protein and DNA. Example 2 is directed in-line dilution of concentrated buffers.

Abbreviations and Definitions

| Abbreviation | Text |
|---|---|
| ANP | Analytical Procedure |
| CIP | Clean in Place |
| $DBC_{10\%}$ | Dynamic Binding Capacity at 10% breakthrough |
| DPD | Downstream Process Development |
| HCP | Host Cell Protein |
| HMW | High Molecular Weight |
| LEP | Laboratory Experimental Protocol |
| LMW | Low Molecular Weight |
| N/A | Not applicable |
| PA-HPLC | Protein A HPLC |
| PR | Protocol |
| Res. DNA | Residual DNA |
| RT | Room Temperature |

TABLE 4

Buffers used for the studies

| No. | Name | | Item no. | | Used for |
|---|---|---|---|---|---|
| Buffer A | 16% Ethanol | | HPW | 1-0003 | Storage of chromatography |
| | 16.7% of 96% Ethanol | | 96% ethanol | C0866 | systems and column |
| | | | | | Packing of columns |
| Buffer B | 0.1M Sodium Hydroxide | | HPW | 1-0003 | Column CIP |
| | 0.399% Sodium Hydroxide | | NaOH | 1-0080 | pH adjustment of buffers |
| Buffer C | 0.1M Sodium Chloride | | HPW | 1-0003 | HETP equilibration |
| | 0.583% Sodium Chloride | | NaCl | 1-0026 | |
| Buffer D | 0.5M Sodium Chloride | | HPW | 1-0003 | HETP test |
| | 2.87% Sodium Chloride | | NaCl | 1-0026 | |
| Buffer E | 20 mM sodium phosphate, 150 mM NaCl, pH 7.0 ± 0.2 | | HPW | 1-0003 | Equilibration, wash, end elution, wash after elution |
| | 0.205% di-sodium hydrogen phosphate•$2H_2O$ | | Di-sodium hydrogen phosphate•$2H_2O$ | 1-0047 1-0266 | |
| | 0.132% sodium di-hydrogen phosphate•$2H_2O$ | | Sodium di-hydrogen phosphate•$2H_2O$ | 1-0026 | |
| | 0.877% sodium chloride | | NaCl | | |
| Buffer F | 20 mM citrate, 100 mM NaCl, pH 3.4 ± 0.2 | | HPW | 1-0003 | Elution |
| | 0.138% tri-sodium citrate•2H2O | | Tri-sodium citrate•2H2O | 1-0187 1-0416 | |
| | 0.294% citric acid, anhydrous | | Citric acid, anhydrous | 1-0026 | |
| | 0.585% sodium chloride | | NaCl | | |
| Buffer G | 20 mM citrate, 100 mM NaCl, pH 6.0 ± 0.2 | | HPW | 1-0003 | Dilution of eluate |
| | 0.514% tri-sodium citrate•2H2O | | Tri-sodium citrate•2H2O | 1-0187 1-0416 | |
| | 0.049% citric acid, anhydrous | | Citric acid, anhydrous | 1-0026 | |
| | 0.585% sodium chloride | | NaCl | | |
| Buffer H | 1.0M Bis Tris, pH 10.0 | | HPW | 1-0003 | pH adjustment |
| | 11.8% Bis Tris | | Bis Tris | 1-0519 | |
| Buffer I | 1M Sodium Hydroxide (technical quality) | | HPW | 1-0003 | CIP of Äkta-system, buffer pH adjustment |
| | 12.5% of 32% Sodium Hydroxide | | NaOH | C3567-COA | |
| Buffer J | 1% Nitric acid | | HPW | 1-0003 | CIP of Äkta-system |
| | 1.45% of 69% Nitric acid | | $HNO_3$ | 1-0108 | |
| Buffer K | 0.1M Phosphoric Acid | | HPW | 1-0003 | Column CIP, ProVance |
| | 0.98% Phosphoric Acid of 85% | | $H_3PO_4$ | 1-0063 | |
| Buffer B10 | 1M Sodium Hydroxide | | HPW | 10 | Column CIP |
| | 3.99% Sodium Hydroxide | | NaOH | | pH adjustment of buffers |
| Buffer E10 | 200 mM sodium phosphate, 1.5M NaCl, pH 7.0 ± 0.2 | | HPW | 10 | Equilibration, wash, end elution, wash after elution |
| | 1.51% di-sodium hydrogen phosphate•$2H_2O$ | | Di-sodium hydrogen phosphate•$2H_2O$ | | |
| | 1.80% sodium di-hydrogen phosphate•$2H_2O$ | | Sodium di-hydrogen phosphate•$2H_2O$ | | |
| | 8.77% sodium chloride | | NaCl | | |
| Buffer F10 | 200 mM citrate, 1.0M NaCl, pH 3.4 ± 0.2 | | HPW | 10 | Elution |
| | 1.38% tri-sodium citrate•2H2O | | Tri-sodium citrate•2H2O | | |
| | 2.94% citric acid, anhydrous | | Citric acid, anhydrous | | |
| | 5.85% sodium chloride | | NaCl | | |
| Buffer B-Dil | 0.1M Sodium Hydroxide | | Buffer B10 | 1:10 | Column CIP |
| | 10% Buffer B10 | | HPW | | pH adjustment of buffers |
| | 90% HPW | | | | |

TABLE 4-continued

Buffers used for the studies

| No. | Name | Item no. | | Used for |
|---|---|---|---|---|
| Buffer E-Dil | 20 mM sodium phosphate, 150 mM NaCl, pH 7.0 ± 0.2 10% Buffer E10 90% HPW | Buffer E10 HPW | 1:10 | Equilibration, wash, end elution, wash after elution |
| Buffer F-Dil | 20 mM citrate, 100 mM NaCl, pH 3.4 ± 0.2 10% Buffer F10 90% HPW | Buffer F10 HPW | 1:10 | Elution |

Example 1

The purpose of this experiment was to purify material from bioreactors using a Protein A Chromatography column at normal and overloaded conditions. The Quantitative and qualitative output was evaluated for the two setups at room temperature and at 35° C. simulating capturing of product directly from the bioreactor.

Two different Protein A resins were tested:
MabSelect SuRe from GE Health Care based on an Agarose gel. Column CIP performed by 0.1 M Sodium Hydroxide.
ProVance from Grace based on a Silica matrix mainly for single campaign-use chromatography. Column CIP performed by 0.1 M Phosphoric Acid.

As the Protein A Chromatography step is the first step of normally three steps with separation power, any remaining impurity (aggregate, HCP and res. DNA) will be reduced by the subsequent process steps.

Process Description

The overall scope was to establish a continuously chromatographic setup combining two columns according to the present invention used for overload chromatography e.g. combined with a bioreactor using continuously harvesting by perfusion technology.

The tests described in this protocol examined the performance of a column by the conditions described in Table 1 below.

| Experiment | Resin | Loading | Temperature | LEP no. # |
|---|---|---|---|---|
| 1 | MabSelect SuRe from GE | Overloading with 20-40% break through Set point: 49 mg/mL | Room temperature | LEP. 2802 |
| 2 | | Overloading with 20-40% break through Set point: 49 mg/mL | 35° C. | LEP. 2621 |
| 3 | | Normal load at 70-80% of maximum DBC Set point: 28 mg/mL | Room temperature | LEP. 2622 |
| 4 | | Overloading with 20-40% break through Set point: 60 mg/mL | Room temperature | LEP. 2919 |
| 5 | | Overloading with 20-40% break through Set point: 60 mg/mL | 35° C. | LEP. 2920 |
| 6 | ProVance from Grace | Overloading with 20-40% break through Set point: 68 mg/mL | Room temperature | LEP. 2803 |
| 7 | | Normal load at 70-80% of maximum DBC Set point: 39 mg/mL | Room temperature | LEP. 2804 |

Equipment

The Protein A Chromatography runs were performed using Äkta Explorer, pH meter, Conductivity meter, NanoDrop for determination of protein concentration by OD280 and balances Methods Test of Protein A Chromatography The parameter settings for the Protein A Chromatography CIP-cycles and chromatography runs are shown in the tables below.

Parameter settings

| Parameter description | Parameter set points | Unit |
|---|---|---|
| Default linear flow - CIP | 200[1] | cm/h |
| Flow direction | Downflow | N/A |

[1]Flow for ProVance was adjusted to 100 cm/h to maintain a constant contact time MabSelect SuRe CIP procedure before run

| CIP procedure | Phase name | Inlet | Outlet |
|---|---|---|---|
| 3 CV of buffer B[1] (downflow) | CIP | B1 | F1 |
| No Pause | — | — | — |
| 5 CV of buffer E (upflow) | Equilibration | A11 | F1 |

[1]Buffer K used for CIP of ProVance

Parameter setting for

| Parameter description | Parameter set points | Unit |
|---|---|---|
| Column flow direction - equilibration and run | Upflow | N/A |
| Column flow direction - Sanitization | Downflow | N/A |
| Default linear flow - equilibration and wash | (5.8 mL/min) 350[1] | cm/h |
| Default linear flow - load and elution | (3.3 mL/min) 200[2] | cm/h |
| Target of Load | See table 1 | mg/mL resin |

[1]Flow for ProVance was adjusted to 175 cm/h to maintain a constant contact time
[2]Flow for ProVance was adjusted to 100 cm/h to maintain a constant contact time MabSelect SuRe chromatographic procedure

| Chromatographic procedure | Phase name | Inlet | Outlet |
|---|---|---|---|
| 2 CV of buffer E - Autozero after 1.9 CV | Equilibration | A11 | F1 |
| Load product | Load | A15 | [1] |
| 30 CV of buffer E | Wash[2] | A11 | F1 [1] |
| 15 CV of buffer F | Elution | A13 | F2 |

-continued

| Chromatographic procedure | Phase name | Inlet | Outlet |
|---|---|---|---|
| Collection: Start ≥ 100 mAU. End ≤ 100 mAU | | | |
| 5 CV of buffer E | Equilibration | A11 | F1 |

[1] Load and the two first CV's of wash is collected in suitable fractions to enable determination of the Dynamic Binding Capacity
[2] 2 CV at 200 cm/h followed by 28 CV at 350 cm/h Test of Protein A Chromatography The sampling setup for the Protein A Chromatography runs are shown in Table 5 below.

| | pH | Conductivity | Conc. By OD280 | PA-HPLC | SE-UPLC | Res. DNA[1] ANP no | HCP | Res. ProA | SDS PAGE (Red) | SDS PAGE (Non-Red) |
|---|---|---|---|---|---|---|---|---|---|---|
| | DPD | DPD | DPD | CMC00853 | CMC08266 | CMC02095 | CMC00747 | CMC05331 | CMC00048 | CMC00329 |
| Sample Volume (mL) | | | | | 1 | 2 | 1 | 1 | 1 | 1 |
| Storage condition | +5° C. | | | | | | −80° C. | | | |
| Load sample | x | x | | x | | | | | x | x |
| Flow through | | | | x | | | | | | |
| Protein A Chromatography after neutralization and filtration | x | x | x | x | x | 2x | x | x | x | x |

Test of MabSelect SuRe Protein A Chromatography.

Chromatographic profiles for Protein A Chromatography with MabSelect SuRe at overload and normal load were obtained (not shown).

The chromatographic profiles (not shown) of the MabSelect SuRe runs performed as expected with the following comments:

Length of load peak for the overload runs was as expected longer than the load peak for the normal load.

Length of wash fraction was increased to 30 CV to ensure sufficient washout of unbound material. The length of the wash will be reduced in further experiments to the length needed to achieve the required reduction of unbound material.

The volume and height of the elution peak were;
36.7 mL and 3.15 AU for the normal load run (LEP2622),
40.4 mL and 3.20 AU for the overload run (LEP2802) and
39.1 mL and 3.29 AU for the overload run (LEP2621) storage of load at 35° C.
39.7 mL and 2.9 AU for the overload run (LEP2919).
39.7 mL and 2.9 AU for the overload run (LEP2920) loaded at 35° C.
(Peak height was not visualizing the actual peak height as the AU-values are above the max. of the UV-monitor).

No significant difference in yield and purity was observed by loading at room temperature or 35° C., which simulates loading harvest from perfusion directly to the column.

The Dynamic Binding Capacity at 10% ($DBC_{10\%}$) breakthrough was approx. 48 mg/mL resin.

Test of ProVance Protein A Chromatography.

Chromatographic profiles for Protein A Chromatography with ProVance at overload and normal load were obtained (not shown). The chromatographic profiles of for the ProVance runs were similar to MabSelect SuRe runs and performed as expected with the following comments:

Length of wash fraction was increased to 30 CV to ensure sufficient washout of unbound process liquid. The length of the wash will be reduced to the length needed to achieve the required reduction of unbound material.

The volume and height of the elution peak was;
9.4 mL and 2.96 AU for the normal load run (LEP2804),
13.6 mL and 3.05 AU for the overload run (LEP2803).
Peak height is not visualizing the actual peak height as the AU-values are above the max. of the UV-monitor.

The Dynamic Binding Capacity at 10% ($DBC_{10\%}$) breakthrough is approx. 41 mg/mL resin.

Analytical data generated for quantitative and qualitative evaluation of the Protein A Chromatography runs are listed in Table 6. The data are commented below for each type of resin:

MabSelect SuRe:
  Maximum amount of product loaded on MabSelect SuRe during overload runs was 45 to 49 mg/mL resin, which vary due to variation on the PA-HPLC assay. $DBC_{10\%}$ was 48 mg/mL resin for MabSelect SuRe.
  Yields for these runs were between 85 and 107%; in average 95% and depended on the variation on quantification of the load by PA-HPLC and eluate by OD280.
  Product recovery for the normal load run was 25.8 mg/mL resin resulting in a yield at 101%.
  The Size Exclusion profile of the eluates from the normal and overload runs were similar.
  The pattern for product and impurities detected by reduced SDS PAGE and non-reduced SDS PAGE, were similar.
  The process related impurities; relative HCP, residual DNA and residual Protein A are all at the same level.
  No major difference in yield and purity by loading at room temperature or 35° C. However, a major reduction in residual DNA contamination in host cell protein when loading at 35° C. was observed.

ProVance:
  Product recovery on ProVance during overload runs was 38 mg/mL resin, which was approx. 20% lower than the capacity of MabSelect SuRe. $DBC_{10\%}$ is 41 mg/mL resin for ProVance.
  Yields for overload—as well as normal-run were 95%, which was at a similar level compare to runs with MabSelect SuRe.

The Size Exclusion profile (monomer/HMW/LMW) of the eluates is 94.0/3.6/2.4% for the normal run and 92.6/4.8/2.5% for the over load run.

The pattern for product and impurities detected by reduced SDS PAGE and non-reduced SDS PAGE, show similarity (see Appendix 1 and Appendix 2)

The process related impurities; relative HCP, residual DNA and residual Protein A are all at the same level.

Table 6: Analytical data generated for quantitative and qualitative evaluation of Protein A Chromatography.

A chromatography run using ProVance in normal mode (LEP2803) resulted in a product recovery of 31.1 mg/mL resin and in overload mode (LEP2804) of 38.3 mg/mL, which is an increase in product load capacity of 23%.

In addition, the chromatography run (LEP2920) where both the load and the column were placed in a thermo cabinet at 35° C. resulted in a 50% reduction in residual DNA contamination (735 pg/mL compared to 1492 pg/mL) and a 24% reduction in host cell protein 118 ng/mL compared to 156 ng/mL.

| | | | | | Analytical procedure: | | | | |
|---|---|---|---|---|---|---|---|---|---|
| | Ref. | Mode | Load ratio | Product recovery | Temp ANP no | Yield | Conc. By OD280 | PA-HPLC | SE-UPLC, Purity |
| Type of resin | — | — | mg/mL resin | mg/mL resin | ° C. | % | DPD mg/mL | CMC00853 mg/mL | CMC08266 % |
| MabSelect SuRe | LEP2621 | Overload | 44.9 | 47.9 | 35[2] | 107% | 6.2 | 6.7 | 93.7 |
| MabSelect SuRe | LEP2622 | Normal load | 25.8 | 26.0 | RT | 101% | 3.7 | 3.7 | 94.1 |
| MabSelect SuRe | LEP2802 | Overload | 49.1 | 43.5 | RT | 89% | 6.1 | 6.6 | 93.8 |
| MabSelect SuRe | LEP2919 | Overload | 49.4 | 45.0 | RT | 91% | 6.4 | 6.9 | 94.8 |
| MabSelect SuRe | LEP2920 | Overload | 52.7[5] | 44.7 | 35[3] | 85% | 5.6 | 5.9 | 94.2 |
| ProVance | LEP2803 | Overload | 39.8 | 38.3 | RT | 96% | 5.0 | 5.0 | 92.6 |
| ProVance | LEP2804 | Normal load | 32.8 | 31.1 | RT | 95% | 4.6 | 4.5 | 94.0 |

| | | | | Analytical procedure: | | | | |
|---|---|---|---|---|---|---|---|---|
| | SE-UPLC, HMW | SE-UPLC, LMW | Res. DNA | Relative Res. DNA ANP no | HCP | Relative HCP | Res. ProA | Relative Res. ProA |
| Type of resin | CMC08266 % | CMC08266 % | CMC02095 pg/mL | CMC02095 pg/mg | CMC00747 ng/mL | CMC00747 ng/mg | CMC05331 ng/mL | CMC05331 ng/mg |
| MabSelect SuRe | 4.2 | 2.1 | 2538.0 | 378.8 | 193.0 | 28.8 | <20 | <4.2 |
| MabSelect SuRe | 3.8 | 2.1 | 1492.0 | 403.2 | 156.0 | 42.2 | <10 | <2.7 |
| MabSelect SuRe | 4.1 | 2.1 | N/A | N/A | 195.0 | 29.5 | <10 | <1.5 |
| MabSelect SuRe | 3.5 | 1.7 | N/A | N/A | 228 | 33.0 | <130 | <18.8 |
| MabSelect SuRe | 4.1 | 1.7 | N/A | N/A | 118 | 20.0 | <130 | <22.0 |
| ProVance | 4.8 | 2.5 | 1098.0 | 219.6 | 178.0 | 35.6 | <10 | <2.0 |
| ProVance | 3.6 | 2.4 | 2401.0 | 533.6 | 158.0 | 35.1 | <10 | <2.2 |

[1] C: Compare to reference
[2] Load stored at 35° C., but as column and tubing were stored at room temperature, the temperature of the load has decreased significantly before reaching the column.
[3] Column and load was stored in Thermo Cabinet at 35° C.
[5] Loading was increased to enable higher binding to the resin, which result in lower yield. Flow through calculated based on an average of product concentration of the fractions

CONCLUSION

Overload and normal load chromatography runs were conducted using an agarose based gel (MabSelect SuRe) and a silica based resin (ProVance) resulting in similar yields and purity (see Table 6).

However, running the MabSelect SuRe (LEP2622) in normal mode, the product recovery was 26.0 mg/mL resin and in overload mode (LEP2621; 47.9 mg/mL resin), (LEP2802; 43.5 mg/mL resin), (LEP2919; 45.0 mg/mL resin) and (LEP2920; 44.7 mg/mL resin), respectively. Accordingly, running the MabSelect SuRe column in overload mode resulted in a product recovery of 65 to 85% higher than running in normal mode.

Example 2

The purpose of this example was to establish a setup with in-line dilution of concentrated buffers, in this case with 10 times concentration of the original buffer according to the present invention.

The tests described in this example will examine the preparation of the concentrated buffers and comparison after dilution with the original buffer described in Table 2.

TABLE 2

Test setup for preparing of concentrated buffers.

| Activity | Description |
|---|---|
| 1 | Prepare each original buffers three times for MabSelect SuRe chromatography (see Table 4) in order to establish a good reference for pH and conductivity |
| 2 | Prepare concentrated buffers (see Table 4) |
| 3 | Prepare diluted buffers based on concentrated buffers (see Table 4) to compare with original buffers and measure amount of NaOH/HCl to be used for pH-adjustment |
| 4 | Adjust concentrated buffers (according to required acid/base used at "3" to reach target), recalculate composition of concentrated buffers, update buffer sheets of relevant concentrated buffers and repeat experiment 2 and 3. |
| 5 | Test of in-line dilution of final concentrated buffers e.g. by use of Äkta Avant to compare with original buffers. |

TABLE 3

Test conditions of experiments for concentrated buffers

| Experiment | Buffer | Purpose | Composition | LEP no. # |
|---|---|---|---|---|
| 1 | B | Column | 0.1M Sodium Hydroxide | LEP. 2733 |
| 2 | B10 | CIP | 1M Sodium Hydroxide | LEP. 2733 |
| 3 | B-Dil | | 0.1M Sodium Hydroxide by: 10% Buffer B10, 90% HPW | LEP. 2733 |
| 4 | E | Equilibration | 20 mM sodium phosphate, 150 mM NaCl, pH 7.0 ± 0.2 | LEP. 2733 |
| 5 | E10 | and wash | 200 mM sodium phosphate, 1.5M NaCl, pH "7.0" ± 0.2 | LEP. 2733 |
| 6 | E-Dil | | 20 mM sodium phosphate, 150 mM NaCl, pH 7.0 ± 0.2 by: 10% Buffer E10, 90% HPW | LEP. 2733 |
| 7 | F | Elution | 20 mM citrate, 100 mM NaCl, pH 3.4 ± 0.2 | LEP. 2733 |
| 8 | F10 | | 200 mM citrate, 1.0M NaCl, pH "3.4" ± 0.2 | LEP. 2733 |
| 9 | F-Dil | | 20 mM citrate, 100 mM NaCl, pH 3.4 ± 0.2 by: 10% Buffer F10, 90% HPW | LEP. 2733 |

Test of Concentrated Buffers

Three concentrated buffers, which are central for the chromatography, were prepared at 10 times the normal buffer concentration. These were buffers B10, E10 and F10 (see Table 4 above) used for column CIP, equilibration and elution respectively. The specific procedure for development of concentrated buffers includes:
1. Prepare original buffer in triplicate
   Measure in triplicate pH, conductivity and if relevant other relevant parameter of buffer
2. Prepare concentrated buffer
   Measure pH, conductivity and if relevant other relevant parameter of concentrated buffer
3. Dilute concentrated buffer to the original concentration
   Measure pH, conductivity and if relevant other relevant parameter of diluted buffer
4. Compare the original and diluted buffer and determine the off-set of pH
5. Determine the off-set of pH in the concentrated buffer
6. Prepare concentrated buffer after adjustment for the off-set
7. Repeat point 3. If pH is within acceptance criteria, the concentrated buffer is approved. Otherwise repeat step 4 to 6.

The pH-value of the original buffer is the set point for buffer, which is prepared based on a concentrated buffer. The success criterion for preparation of a concentrated buffer is that the pH-value of this buffer after dilution has the same pH-value as the original buffer±0.2. The conductivity is used as control of a correct composition of buffer components, which is likely when the conductivity is within range compare to the original buffer.

The pH of the concentrated buffer is corrected if needed by measuring the off-set in a diluted buffer and the amount of acid or base used for adjusting pH to set point of the diluted buffer. The same amount of acid or based used to adjust 1 L diluted buffer was added to 100 mL concentrated buffer. Thereby the correct pH of the concentrated buffer was determined and a buffer composition resulting in this pH-value was established by use of a standard buffer tool. Testing.

Concentrated buffers, at 10 times the normal buffer concentration were prepared for the buffers shown in Table 7.

TABLE 7

Buffers used as models for preparation of concentrated buffers.

| No. | Name |
|---|---|
| Buffer B | 0.1M Sodium Hydroxide |
| Buffer E | 20 mM sodium phosphate, 150 mM NaCl, pH 7.0 ± 0.2 |
| Buffer F | 20 mM citrate, 100 mM NaCl, pH 3.4 ± 0.2 |

Using specific procedure for development of concentrated buffers discussed above the off-set pH of diluted buffers, based on a 10 times concentrated buffer, was determined. Data for preparation of a 10 times concentrated buffer E (buffer E10) is shown below.
1. 20 mM sodium phosphate, 150 mM NaCl, pH 7.0 is prepared three times pH is measured to 7.02; 7.03 and 7.08 respectively having an average at 7.04 Conductivity is measured to 17.41; 17.56 and 17.58 respectively having an average at 17.52 mS/cm
2. 200 mM sodium phosphate, 1.5 M NaCl, pH 7.0
   Measure pH, conductivity and if relevant other relevant parameter of concentrated buffer
3. Dilute concentrated buffer to the original concentration
   Measure pH, conductivity and if relevant other relevant parameter of diluted buffer
4. Compare the original and diluted buffer and determine the off-set of pH
5. Determine the off-set of pH in the concentrated buffer
6. Prepare concentrated buffer after adjustment for the off-set
7. Repeat point 3. If pH is within acceptance criteria, the concentrated buffer is approved. Otherwise repeat step 4 to 6.

The pH-value of buffer E10 is 6.14 resulting in a pH-value after dilution at 6.83 having a set point at 7.00. This difference in pH between the diluted buffer and the original buffer is on the border of the acceptance criteria, why an adjustment of the concentrated buffer was initiated. Using the specific procedure for development of concentrated buffers discussed above, buffer E10 was corrected resulting in data shown below.

The preparation and adjustment of buffer B10 and F10 was carried out after the same principles (results not shown).

The pH-value of buffer F10 was 2.84 resulting in a pH-value after dilution at 3.25 having a set point at 3.40. This difference in pH between the diluted buffer and the original buffer was on the border of the acceptance criteria, why an adjustment of the concentrated buffer was initiated.

Using the specific procedure for development of concentrated buffers discussed above, buffer F10 was corrected resulting in a pH-value after dilution at 3.49, which is very close to the set point at 3.40.

The conductivity of buffer B10 was 187.2 mS/cm resulting in conductivity after dilution at 22.9 mS/cm. No set point was established but the conductivity of the original buffer was 22.13 mS/cm and accordingly the difference of conductivity between the diluted buffer and the original buffer was very small and no adjustment was carried out.

CONCLUSION

A model for preparing 10 times concentrated buffers to enable a 10 times dilution reaching the pH and conductivity of the original buffer was established. The procedure for pH-adjustment of concentrated buffers, resulting in diluted buffers within the acceptance criteria and very close to the set point of the original buffers, was obtained.

No problem with solubility or precipitation was observed during preparation and storage of concentrate buffers at room temperature.

The invention claimed is:

1. A bioreactor arrangement for producing a biopolymer expressed by a cell, wherein the bioreactor arrangement comprises a bioreactor system and a chromatography system wherein the bioreactor system comprises:
a cell culture vessel (50) for holding a medium comprising the biopolymer and waste products wherein the cell culture vessel (50) comprises a product harvest module (51), wherein the product harvest module (51) has an outlet (16), and
wherein the chromatography system comprises:
a first chromatography unit (2) and a second chromatography unit (3) both comprising material having affinity for the biopolymer, wherein the first chromatography unit (2) has an inlet (12) and an outlet (13) and the second chromatography unit (3) has an inlet (14) and an outlet (15),
wherein the outlet (16) of the product harvest module (51) is in fluid connection with the inlet (12) of the first chromatography unit (2) and in fluid connection with the inlet (14) of the second chromatography unit (3),
wherein a first valve means (31) is located between the outlet (16) of the product harvest module and the inlet (12) of the first chromatography unit (2), and a second valve means (32) is located between the outlet (16) of the product harvest module and the inlet (14) of the second chromatography unit (3),
wherein the outlet (13) of the first chromatography unit (2) is in direct fluid connection with the inlet (14) of the second chromatography unit (3), and a third valve means (33) is located between the outlet (13) of the first chromatography unit (2) and the inlet (14) of the second chromatography unit (3), and the outlet (15) of the second chromatography unit (3) is in direct fluid connection with the inlet (12) of the first chromatography unit (2), and a fourth valve means (34) is located between the outlet (15) of the second chromatography unit (3) and the inlet (12) of the first chromatography unit (2), wherein biopolymer that is present in a flow-through from the first chromatography unit (2) is directly captured on the second chromatography unit (3), and biopolymer that is present in a flow-through from the second chromatography unit (3) is directly captured on the first chromatography unit (2) and wherein the bioreactor system of said bioreactor arrangement further comprises at least one of (a) a medium container (53) in fluid connection with the cell culture vessel (50) or (b) a buffer supply (55) in fluid connection with the cell culture vessel (50).

2. The bioreactor arrangement of claim 1, wherein the bioreactor system further comprises an inline medium dilution system (56) for diluting concentrated medium from the medium container (53), the inline medium dilution system having an inlet (57) and an outlet (58), wherein the inlet (57) is in fluid connection with the medium container (53) and the inlet (57) is in fluid connection with the water/buffer supply (55), and wherein the outlet (58) of the inline medium dilution system (56) is in fluid connection with the cell culture vessel (50).

3. The bioreactor arrangement of claim 1, wherein the chromatography system further comprises,
a wash buffer container (4), having an outlet (21),
an elution buffer container (5), having an outlet (22),
optionally a cleaning buffer container (6), having an outlet (23)
optionally an equilibration buffer container (7), having an outlet (24),
wherein the outlet (21) of the wash buffer container (4) is in fluid connection with the inlet (12) of the first chromatography unit (2) and wherein a twelfth valve means (40b) is located between the outlet (21) of the wash buffer container (4) and the inlet (12) of the first chromatography unit (2), wherein the outlet (21) of the wash buffer container (4) is in fluid connection with the inlet (14) of the second chromatography unit (3) and wherein a thirteenth valve means (41b) is located between the outlet (21) of the wash buffer container (4) and the inlet (14) of the second chromatography unit 3),
wherein the outlet (22) of the elution buffer container (5) is in fluid connection with the inlet (12) of the first chromatography unit (2) and wherein a twelfth valve means (40b) is located between the outlet (21) of the elution buffer container (5) and the inlet (12) of the first chromatography unit (2), wherein the outlet (22) of the elution buffer container (5) is in fluid connection with the inlet (14) of the second chromatography unit (3) and wherein a thirteenth valve means (41b) is located between the outlet (22) of the elution buffer container (5) and the inlet (14) of the second chromatography unit 3),
optionally, wherein the outlet (23) of the cleaning buffer container (6) is in fluid connection with the inlet (12) of the first chromatography unit (2) and wherein a twelfth valve means (40b) is located between the outlet (23) of the cleaning buffer container (6) and the inlet (12) of the first chromatography unit (2), wherein the outlet (23) of the cleaning buffer container (6) is in fluid connection with the inlet (14) of the second chromatography unit (3) and wherein a thirteenth valve means (41b) is located between the outlet (23) of the cleaning buffer container (6) and the inlet (14) of the second chromatography unit 3),
optionally, wherein the outlet (24) of the equilibration buffer container (7) is in fluid connection with the inlet (12) of the first chromatography unit (2) and wherein a twelfth valve means (40b) is located between the outlet (24) of the equilibration buffer container (7) and the inlet (12) of the first chromatography unit (2), wherein the outlet (24) of the equilibration buffer container (7) is in fluid connection with the inlet (14) of the second chromatography unit (3) and wherein a thirteenth valve means (41b) is located between the outlet (24) of the equilibration buffer container (7) and the inlet (14) of the second chromatography unit (3).

4. The bioreactor arrangement of claim 1, wherein the chromatography system further comprises,
a wash buffer container (4), having an outlet (21),
an elution buffer container (5), having an outlet (22),
optionally a cleaning buffer container (6), having an outlet (23)
optionally an equilibration buffer container (7), having an outlet (24),
a water supply (8), having an outlet (25) and an inline buffer dilution system (9) having an inlet (26a) and an outlet (27),
wherein the outlet (21) of the wash buffer container (4) is in fluid connection with the inlet (26a) of the inline buffer dilution system (9) and wherein a fifth valve means (35) is located between the outlet (21) of the wash buffer container (4) and the inlet (26a) of the inline buffer dilution system (9),
wherein the outlet (22) of the elution buffer container (5) is in fluid connection with the inlet (26a) of the inline buffer dilution system (9) and wherein a sixth valve means (36) is located between the outlet (22) of the elution buffer container (5) and the inlet (26a) of the inline buffer dilution system (9),
optionally, wherein the outlet (23) of the cleaning buffer container (6) is in fluid connection with the inlet (26a) of the inline buffer dilution system (9) and wherein a seventh valve means (37) is located between the outlet (23) of the cleaning buffer container (6) and the inlet (26a) of the inline buffer dilution system (9),
optionally, wherein the outlet (24) of the equilibration buffer container (7) is in fluid connection with the inlet (26a) of the inline buffer dilution system (9) and wherein an eighth valve means (38) is located between the outlet (24) of the equilibration buffer container (7) and the inlet (26a) of the inline buffer dilution system (9),
wherein the outlet (25) of the water supply (8) is in fluid connection with the inlet (26a) of the inline buffer dilution system (9) or is in fluid connection with a separate inlet (26b) of the inline buffer dilution system (9) and wherein a ninth valve means (39) is located between the outlet (25) of the water supply (8) and the inlet (26a) or the separate inlet (26b) of the inline buffer dilution system (9); and wherein the outlet (27) of the inline buffer dilution system (9) is in fluid connection with the inlet (12) of the first chromatography unit (2) and in fluid connection with the inlet (14) of the second chromatography unit (3), wherein a tenth valve means (40) is located between the outlet (27) of the inline buffer dilution system (9) and the inlet (12) of the first chromatography unit (2), and an eleventh valve means (41) is located between the outlet (27) of the inline buffer dilution system (9) and inlet (14) of the second chromatography unit (3).

5. A bioreactor arrangement for producing a biopolymer expressed by a cell, wherein the bioreactor arrangement comprises a bioreactor system and a chromatography system wherein the bioreactor system comprises:
a cell culture vessel (50) for holding a medium comprising the biopolymer and waste products wherein the cell culture vessel (50) comprises a product harvest module (51), wherein the product harvest module (51) has an outlet (16), and
wherein the chromatography system comprises:
a first chromatography unit (2) and a second chromatography unit (3) both comprising material having affinity for the biopolymer, wherein the first chromatography unit (2) has an inlet (12) and an outlet (13) and the second chromatography unit (3) has an inlet (14) and an outlet (15),
wherein the outlet (16) of the product harvest module (51) is in fluid connection with the inlet (12) of the first chromatography unit (2) and in fluid connection with the inlet (14) of the second chromatography unit (3),
wherein a first valve means (31) is located between the outlet (16) of the product harvest module and the inlet (12) of the first chromatography unit (2), and a second valve means (32) is located between the outlet (16) of the product harvest module and the inlet (14) of the second chromatography unit (3),
wherein the outlet (13) of the first chromatography unit (2) in the absence of a holding tank is in fluid connection with the inlet (14) of the second chromatography unit (3), and a third valve means (33) is located between the outlet (13) of the first chromatography unit (2) and the inlet (14) of the second chromatography unit (3), and the outlet (15) of the second chromatography unit (3) in the absence of a holding tank is in fluid connection with the inlet (12) of the first chromatography unit (2), and a fourth valve means (34) is located between the outlet (15) of the second chromatography unit (3) and the inlet (12) of the first chromatography unit (2), wherein biopolymer that is present in a flow-through from the first chromatography unit (2) in the absence of a holding tank is captured on the second chromatography unit (3), and biopolymer that is present in a flow-through from the second chromatography unit (3) in the absence of a holding tank is captured on the first chromatography unit (2).

6. The bioreactor arrangement according to claim 5, wherein the outlet (13) of the first chromatography unit (2) in the absence of a holding tank is in direct fluid connection with the inlet (14) of the second chromatography unit (3), and a third valve means (33) is located between the outlet (13) of the first chromatography unit (2) and the inlet (14) of the second chromatography unit (3), and the outlet (15) of the second chromatography unit (3) in the absence of a holding tank is in direct fluid connection with the inlet (12) of the first chromatography unit (2), and a fourth valve means (34) is located between the outlet (15) of the second chromatography unit (3) and the inlet (12) of the first chromatography unit (2), wherein biopolymer that is present in a flow-through from the first chromatography unit (2) in the absence of a holding tank is directly captured on the second chromatography unit (3), and biopolymer that is present in a flow-through from the second chromatography unit (3) in the absence of a holding tank is directly captured on the first chromatography unit (2).

7. The bioreactor arrangement of claim 5, wherein the bioreactor system further comprises an inline medium dilution system (56) for diluting concentrated medium from the medium container (53), the inline medium dilution system having an inlet (57) and an outlet (58), wherein the inlet (57) is in fluid connection with a medium container (53) and the inlet (57) is in fluid connection with a water/buffer supply (55), and wherein the outlet (58) of the inline medium dilution system (56) is in fluid connection with the cell culture vessel (50).

8. The bioreactor arrangement of claim 5, wherein the chromatography system further comprises,
a wash buffer container (4), having an outlet (21),
an elution buffer container (5), having an outlet (22),
optionally a cleaning buffer container (6), having an outlet (23)

optionally an equilibration buffer container (7), having an outlet (24), wherein the outlet (21) of the wash buffer container (4) is in fluid connection with the inlet (12) of the first chromatography unit (2) and wherein a twelfth valve means (40b) is located between the outlet (21) of the wash buffer container (4) and the inlet (12) of the first chromatography unit (2), wherein the outlet (21) of the wash buffer container (4) is in fluid connection with the inlet (14) of the second chromatography unit (3) and wherein a thirteenth valve means (41b) is located between the outlet (21) of the wash buffer container (4) and the inlet (14) of the second chromatography unit 3), wherein the outlet (22) of the elution buffer container (5) is in fluid connection with the inlet (12) of the first chromatography unit (2) and wherein a twelfth valve means (40b) is located between the outlet (21) of the elution buffer container (5) and the inlet (12) of the first chromatography unit (2), wherein the outlet (22) of the elution buffer container (5) is in fluid connection with the inlet (14) of the second chromatography unit (3) and wherein a thirteenth valve means (41b) is located between the outlet (22) of the elution buffer container (5) and the inlet (14) of the second chromatography unit 3), optionally, wherein the outlet (23) of the cleaning buffer container (6) is in fluid connection with the inlet (12) of the first chromatography unit (2) and wherein a twelfth valve means (40b) is located between the outlet (23) of the cleaning buffer container (6) and the inlet (12) of the first chromatography unit (2), wherein the outlet (23) of the cleaning buffer container (6) is in fluid connection with the inlet (14) of the second chromatography unit (3) and wherein a thirteenth valve means (41b) is located between the outlet (23) of the cleaning buffer container (6) and the inlet (14) of the second chromatography unit 3), optionally, wherein the outlet (24) of the equilibration buffer container (7) is in fluid connection with the inlet (12) of the first chromatography unit (2) and wherein a twelfth valve means (40b) is located between the outlet (24) of the equilibration buffer container (7) and the inlet (12) of the first chromatography unit (2), wherein the outlet (24) of the equilibration buffer container (7) is in fluid connection with the inlet (14) of the second chromatography unit (3) and wherein a thirteenth valve means (41b) is located between the outlet (24) of the equilibration buffer container (7) and the inlet (14) of the second chromatography unit (3).

9. The bioreactor arrangement of claim 5, wherein the chromatography system further comprises,
a wash buffer container (4), having an outlet (21),
an elution buffer container (5), having an outlet (22),
optionally a cleaning buffer container (6), having an outlet (23)
optionally an equilibration buffer container (7), having an outlet (24),
a water supply (8), having an outlet (25) and an inline buffer dilution system (9) having an inlet (26a) and an outlet (27),
wherein the outlet (21) of the wash buffer container (4) is in fluid connection with the inlet (26a) of the inline buffer dilution system (9) and wherein a fifth valve means (35) is located between the outlet (21) of the wash buffer container (4) and the inlet (26a) of the inline buffer dilution system (9),
wherein the outlet (22) of the elution buffer container (5) is in fluid connection with the inlet (26a) of the inline buffer dilution system (9) and wherein a sixth valve means (36) is located between the outlet (22) of the elution buffer container (5) and the inlet (26a) of the inline buffer dilution system (9),
optionally, wherein the outlet (23) of the cleaning buffer container (6) is in fluid connection with the inlet (26a) of the inline buffer dilution system (9) and wherein a seventh valve means (37) is located between the outlet (23) of the cleaning buffer container (6) and the inlet (26a) of the inline buffer dilution system (9),
optionally, wherein the outlet (24) of the equilibration buffer container (7) is in fluid connection with the inlet (26a) of the inline buffer dilution system (9) and wherein an eighth valve means (38) is located between the outlet (24) of the equilibration buffer container (7) and the inlet (26a) of the inline buffer dilution system (9),
wherein the outlet (25) of the water supply (8) is in fluid connection with the inlet (26a) of the inline buffer dilution system (9) or is in fluid connection with a separate inlet (26b) of the inline buffer dilution system (9) and wherein a ninth valve means (39) is located between the outlet (25) of the water supply (8) and the inlet (26a) or the separate inlet (26b) of the inline buffer dilution system (9); and wherein the outlet (27) of the inline buffer dilution system (9) is in fluid connection with the inlet (12) of the first chromatography unit (2) and in fluid connection with the inlet (14) of the second chromatography unit (3), wherein a tenth valve means (40) is located between the outlet (27) of the inline buffer dilution system (9) and the inlet (12) of the first chromatography unit (2), and an eleventh valve means (41) is located between the outlet (27) of the inline buffer dilution system (9) and inlet (14) of the second chromatography unit (3).

* * * * *